(12) United States Patent
Tamura et al.

(10) Patent No.: US 9,442,067 B2
(45) Date of Patent: *Sep. 13, 2016

(54) PLASMON SENSOR AND MANUFACTURING METHOD THEREFOR, AND METHOD FOR INSERTING SAMPLE INTO PLASMON SENSOR

(75) Inventors: Masaya Tamura, Osaka (JP); Hiroshi Kagata, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 258 days.

This patent is subject to a terminal disclaimer.

(21) Appl. No.: 13/260,444

(22) PCT Filed: Apr. 20, 2010

(86) PCT No.: PCT/JP2010/002833
§ 371 (c)(1),
(2), (4) Date: Sep. 26, 2011

(87) PCT Pub. No.: WO2010/122776
PCT Pub. Date: Oct. 28, 2010

(65) Prior Publication Data
US 2012/0028247 A1 Feb. 2, 2012

(30) Foreign Application Priority Data

Apr. 21, 2009 (JP) .................... 2009-102589
Oct. 9, 2009 (JP) .................... 2009-234769

(51) Int. Cl.
*G01N 21/552* (2014.01)
*G01N 33/543* (2006.01)

(52) U.S. Cl.
CPC ....... *G01N 21/553* (2013.01); *G01N 33/54366* (2013.01)

(58) Field of Classification Search
CPC ........... G01N 21/27; G01N 33/54373; G01N 2021/01; G01N 2021/258; G01N 21/553; G02B 5/008
See application file for complete search history.

(56) References Cited

U.S. PATENT DOCUMENTS 6,331,276 B1 * 12/2001 Takei et al. ............... 422/82.09
2003/0036204 A1 * 2/2003 Stark et al. ............... 436/172
(Continued)

FOREIGN PATENT DOCUMENTS

EP    0 805 347 A2    11/1997
JP    10-078393 A    3/1998
(Continued)

OTHER PUBLICATIONS

Yonzon et al., A Comparative Analysis of Localized and Propagating Surface Plasmon Sensors: The Binding of Concanavalin A to a Monosaccharide Functionalized Self-Assembled Monolayer, Sep. 9, 2004, Journal of the American Chemical Society 126, No. 29, pp. 12669-12676.*

(Continued)

*Primary Examiner* — Rebecca Martinez
(74) *Attorney, Agent, or Firm* — RatnerPrestia

(57) ABSTRACT

A plasmon sensor includes a first metal layer and a second metal layer having an upper surface facing a lower surface of the first metal layer. The upper surface of the first metal layer is configured to receive an electromagnetic wave. A hollow space is provided between the first and second metal layers, and is configured to be filled with a test sample containing a medium. This plasmon sensor has a small size and a simple structure.

43 Claims, 26 Drawing Sheets

(56) References Cited

U.S. PATENT DOCUMENTS

2007/0273884 A1* 11/2007 Matsushita et al. .......... 356/445
2009/0109422 A1    4/2009  Handa et al.
2010/0006774 A1    1/2010  Ohtsuka et al.

FOREIGN PATENT DOCUMENTS

| JP | 2003-014765 A | | 1/2003 |
|---|---|---|---|
| JP | 2003-042947 A | | 2/2003 |
| JP | 2005-181296 A | | 7/2005 |
| JP | 2006-322878 A | | 11/2006 |
| JP | 2006-337244 A | | 12/2006 |
| JP | 2007-327948 A | | 12/2007 |
| JP | 2010-019766 A | | 1/2010 |
| WO | WO2007/034395 | * | 3/2007 |
| WO | WO2007/148833 | * | 12/2007 |
| WO | WO 2008/111745 A1 | | 9/2008 |

OTHER PUBLICATIONS

International Search Report for PCT/JP2010/002833, Jul. 27, 2010.
Supplementary European Search Report for EP 10 76 6838, May 26, 2014.
Guang Chen et al., High Sensitivity Biosensor Based on Double Metal-Cladding Waveguide, Proceedings of SPIE, vol. 4904, Jun. 20, 2003
F. Villa et al., Electromagnetic modes in metal-insulator-metal structures, American Physical Society, Physical Review B, vol. 63, No. 16, Apr. 1, 2001.
Xiao-Ping Jin et al., A Novel Nanometeric Plasmonic Refractive Index Sensor, IEEE Transactions on Nanotechnology, IEEE Service Center, Piscataway, NJ, US, vol. 9, No. 2, Mar. 1, 2010.
F. C. Chien et al., A sensitivity comparison of optical biosensors based on four different surface plasmon resonance modes, Biosensors and Bioelectronics, Elsevier BV, NL, vol. 20, No. 3, Oct. 15, 2004.

* cited by examiner

Page 1 of 2

PLASMON SENSOR AND MANUFACTURING METHOD THEREFOR, AND METHOD FOR INSERTING SAMPLE INTO PLASMON SENSOR

This application is a U.S. National Phase application of PCT International Application No. PCT/JP2010/002833.

TECHNICAL FIELD

The present invention relates to a plasmon sensor using surface plasmon resonance adaptable for detecting, e.g. viruses, a method of manufacturing the plasmon sensor, and a method of injecting a test sample into the plasmon sensor.

BACKGROUND ART

FIG. 28 is a sectional view of plasmon sensor 100 adapted for detecting, e.g. viruses which is disclosed in Patent Literature 1. Plasmon sensor 100 includes prism 101, metal layer 102 having a smooth surface disposed under prism 101, insulation layer 103 of a predetermined dielectric constant having a smooth surface and disposed under metal layer 102, and ligands 104 fixed to a lower surface of insulation layer 103.

A surface plasmon wave which is a compression wave of electrons exists on the interface between metal layer 102 and insulation layer 103. Light source 105 located above prism 101 applies p-polarized light to prism 101 under a condition of total reflection. At this moment, an evanescent wave is generated on surfaces of metal layer 102 and insulation layer 103. The light totally reflected on the surface of metal layer 102 enters detector 106 that detects an intensity of the light.

Here, if a matching condition of wave numbers is met under which the wave number of the evanescent wave is consistent with the wave number of the surface plasmon wave is met, energy of the light supplied from light source 105 is used to excite the surface plasmon wave, accordingly decreasing the intensity of the reflected light. The matching condition of wave numbers is dependent upon an incidence angle of the light irradiated from the light source. Therefore, the intensity of the reflected light decreases at a certain incidence angle when measured with detector 106 while changing the incidence angle.

A resonance angle at which the intensity of the reflected light becomes minimum depends on a dielectric constant of insulation layer 103. The dielectric constant of insulation layer 103 changes when an analyte which is a measuring-target substance in a test sample specifically binds to ligands 104 and form a product of specific binding under insulation layer 103, which in turn changes the resonance angle. This allows a binding strength, speed and the like of the specific binding reaction between the analyte and ligands 104 to be detected by monitoring the change in the resonance angle.

Plasmon sensor 100 includes light source 105 for supplying p-polarized light and prism 101 disposed on metal layer 102, thus having a large size and a complex structure.

CITATION LIST

Patent Literature 1: Japanese Patent Laid-Open Publication No. 2005-181296

SUMMARY OF THE INVENTION

A plasmon sensor includes a first metal layer and a second metal layer having an upper surface facing a lower surface of the first metal layer. The upper surface of the first metal layer is configured to receive an electromagnetic wave. A hollow space is provided between the first and second metal layers, and is configured to be filled with a test sample containing a medium.

This plasmon sensor has a small size and a simple structure.

DETAIL DESCRIPTION OF PREFERRED EMBODIMENTS

Exemplary Embodiment 1

Figure 1:
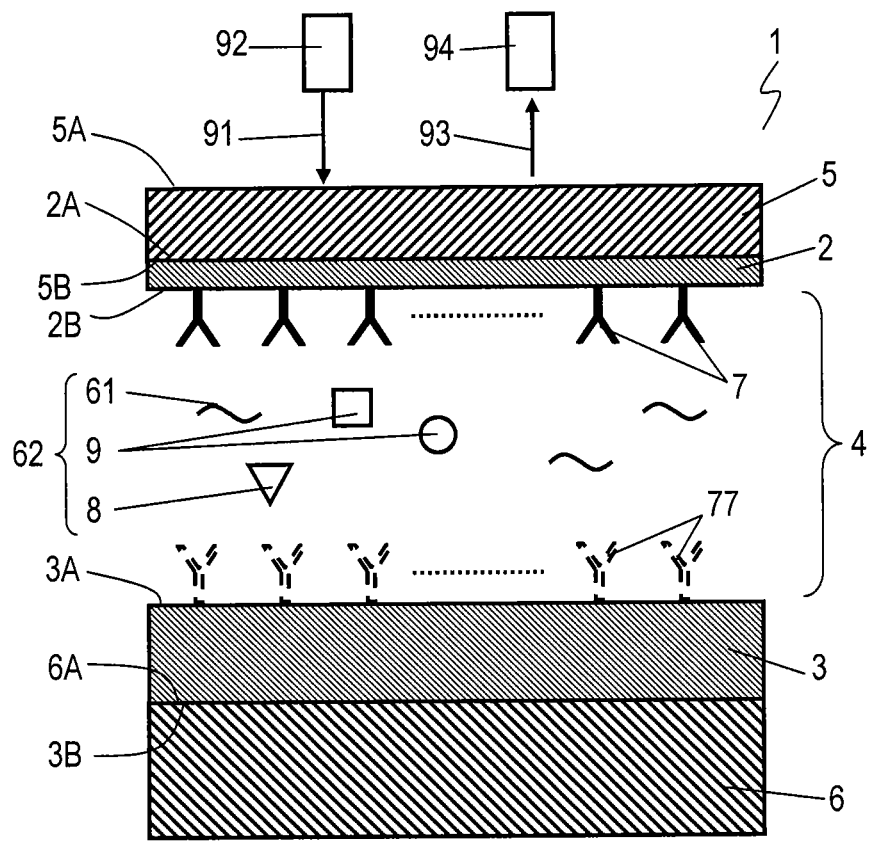
FIG. 1 is a cross-sectional view of a plasmon sensor according to Exemplary Embodiment 1 of the present invention.

FIG. 1 is a cross-sectional view of plasmon sensor 1 according to Exemplary Embodiment 1 of the present invention. Plasmon sensor 1 includes metal layer 2 and metal layer 3 disposed under metal layer 2 facing metal layer 2 across hollow space 4. Metal layers 2 and 3 are made of metal, such as gold or silver. Hollow space 4 can be filled with test sample 62 when plasmon sensor 1 is used, and is sandwiched substantially between metal layers 2 and 3. Test sample 62 contains target analyte 8, other analyte 9, and medium 61. Medium 61 contains a fluid, such as a gas, liquid, or gel, and carries target analyte 8 and other analyte 9.

Metal layer 2, generally having a thickness not larger than 100 nm, cannot maintain its shape by itself. Upper surface 2A of metal layer 2 is therefore fixed onto lower surface 5B of supporter 5 to maintain the shape of metal layer 2. Metal layer 3 is fixed onto and held on upper surface 6A of supporter 6.

Electromagnetic wave 91 enters upper surface 2A of metal layer 2. Metal layer 2, being made of gold, preferably has a thickness within a range from 35 nm to 45 nm when electromagnetic wave 91 is visible light. Thicknesses outside of this range decrease the amount of reflective absorption of electromagnetic wave 91 by the surface plasmon resonance.

Metal layer 3 preferably has a thickness not smaller than 100 nm if made of gold. If the thickness is less than 100 nm, incident electromagnetic wave 91 (i.e., visible light) penetrates metal layer 3, and also decreases the amount of reflective absorption of electromagnetic wave 91 by the surface plasmon resonance.

Plasmon sensor 1 may includes a post or a wall that retains metal layers 2 and 3 in order to maintain a predetermined distance between metal layers 2 and 3. This structure provides plasmon sensor 1 with hollow space 4.

Electromagnetic wave source 92 is placed above upper surface 2A of metal layer 2, or at one side of metal layer 2 opposite to metal layer 3.

Electromagnetic wave source 92 applies electromagnetic wave 91 to metal layer 2 from above upper surface 2A.

An operation of plasmon sensor 1 will be described below. According to Embodiment 1, electromagnetic wave 91 is light, and electromagnetic wave source 92 is a light source. Electromagnetic wave source 92, a light source, does not include any device, such as a polarizing plate, for aligning polarization of light. Unlike conventional plasmon sensor 100 shown in FIG. 28, plasmon sensor 1 of the present invention can excite surface plasmon resonance not only by p-polarized light but also by s-polarized light.

Electromagnetic wave 91 applied to upper surface 2A from above metal layer 2 is supplied to hollow space 4 by penetrating through metal layer 2, and reaches upper surface 3A of metal layer 3. Electromagnetic wave 91 generates surface plasmon on lower surface 2B of metal layer 2 at the side facing hollow space 4, and also on lower surface 3B of metal layer 3 at the side facing hollow space 4. Surface plasmon resonance is excited on lower surface 2B of metal layer 2 when the wave number of electromagnetic wave 91 supplied to hollow space 4 matches with the wave number of the surface plasmon generated on lower surface 2B of metal layer 2. Surface plasmon resonance is also excited on upper surface 3A of metal layer 3 when the wave number of electromagnetic wave 91 matches with that of the surface plasmon generated on upper surface 3A of metal layer 3.

The frequency for generating the surface plasmon resonance can be controlled by adjusting at least one of structural elements which are a shape, mainly a thickness, of metal layer 2, a shape, mainly a thickness, of metal layer 3, a spatial distance between metal layers 2 and 3, a dielectric constant of metal layer 2, a dielectric constant of metal layer 3, a dielectric constant of medium 61 between metal layers 2 and 3, and the distribution of the dielectric constant of medium 61.

Detector unit 94 is placed above upper surface 2A of metal layer 2 for detecting electromagnetic wave 93, such as light. Detector unit 94 receives electromagnetic wave 93, such as the light, reflected or radiated from plasmon sensor 1 when plasmon sensor 1 receives electromagnetic wave 91 delivered from electromagnetic wave source 92.

According to Embodiment 1, the thickness of metal layer 2 is not larger than about 100 nm. If metal layer 2 is thicker than 100 nm, surface plasmon resonance is not excited on any one of lower surface 2B of metal layer 2 and upper surface 3A of metal layer 3 since metal layer 2 prevents the penetrating of a certain wavelength component of the electromagnetic wave (light) that causes the surface plasmon resonance.

Metal layer 2 having the thickness not larger than about 100 nm cannot maintain its shape by itself. Supporter 5 is fixed to upper surface 2A of metal layer 2 in order to maintain the shape of metal layer 2. Supporter 5 is made of a material hardly attenuate electromagnetic wave 91 since supporter 5 needs to transmit electromagnetic wave 91 efficiently to metal layer 2. In Embodiment 2, supporter 5 is made of an optically transparent material, such as a glass or a transparent plastic, that allows light to penetrate through the material efficiently since electromagnetic wave 91 is light. Supporter 5 preferably has a thickness as small as possible practical within a range providing a physical strength.

Metal layer 3 has a thickness not smaller than about 100 nm. Metal layer 3, upon having a thickness less than 100 nm may causes a part of the electromagnetic wave supplied through metal layer 2 to hollow space 4 to leak to outside of hollow space 4 by passing metal layer 3. In other words, this reduces the sensitivity of plasmon sensor 1 when the energy of the electromagnetic wave is lost partially to the outside of hollow space 4 instead of being used for excitation of the surface plasmon resonance as intended. The sensitivity of plasmon sensor 1 can be thus increased by making metal layer 2 thinner than metal layer 3.

The above structure confines electromagnetic wave 91, the light, supplied from electromagnetic wave source 92 into hollow space 4 to excite the surface plasmon resonance. This structure also excites surface plasmon polaritons due to coupling of electromagnetic wave 91 with the surface plasmon, which results in absorption of the supplied electromagnetic wave 91, thereby preventing only a component of absorbed frequency from being radiated while allowing the other frequency components to radiate as electromagnetic wave 93.

Lower surface 3B of metal layer 3 is fixed to upper surface 6A of supporter 6 to retain the shape of metal layer 3.

Electromagnetic wave 91, such as light, supplied to plasmon sensor 1 preferably does not penetrate metal layer 3 in order to increase the sensitivity of plasmon sensor 1. For this reason, supporter 6 is made preferably of a material that cuts off electromagnetic wave 91, such as the light. For example, supporter 6 is made of a metal or a semiconductor having a thickness not smaller than 100 nm.

The thickness of supporter 6 is preferably larger than the thickness of supporter 5 so as to improve physical strength of plasmon sensor 1 as well as to prevent a possible change in the sensing characteristic of plasmon sensor 1 due to deformation of its shape while being used.

In plasmon sensor 1, plural ligands 7 is arranged on lower surface 2B of metal layer 2 at the side facing hollow space 4. Ligands 77 may be provided on upper surface 3A of metal layer 3 at the side facing hollow space 4 similarly to ligands 7, or only ligands 77 can be provided on upper surface 3A of metal layer 3 while ligand 7 may not necessarily be provided on lower surface 2B of metal layer 2 between surfaces 2B and 3A of metal layers 2 and 3.

Figure 2:
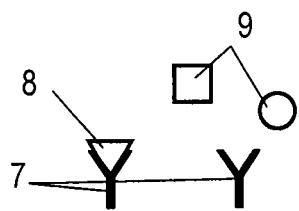
FIG. 2 is a schematic view of the plasmon sensor according to Embodiment 1 for illustrating specific binding between an analyte and ligands.

Ligands 7 specifically bind analyte 8 when test sample 62 containing analyte 8 contacts ligands 7. FIG. 2 is a schematic view for illustrating the specific binding between ligand 7 and analyte 8. Test sample 62 contains analyte 9 representing a non-specific analyte and analyte 8 representing a target analyte. Ligand 7 of an antibody selectively makes specific binding only with analyte 8, but does not make specific binding with non-specific analyte 9.

Figure 3A:
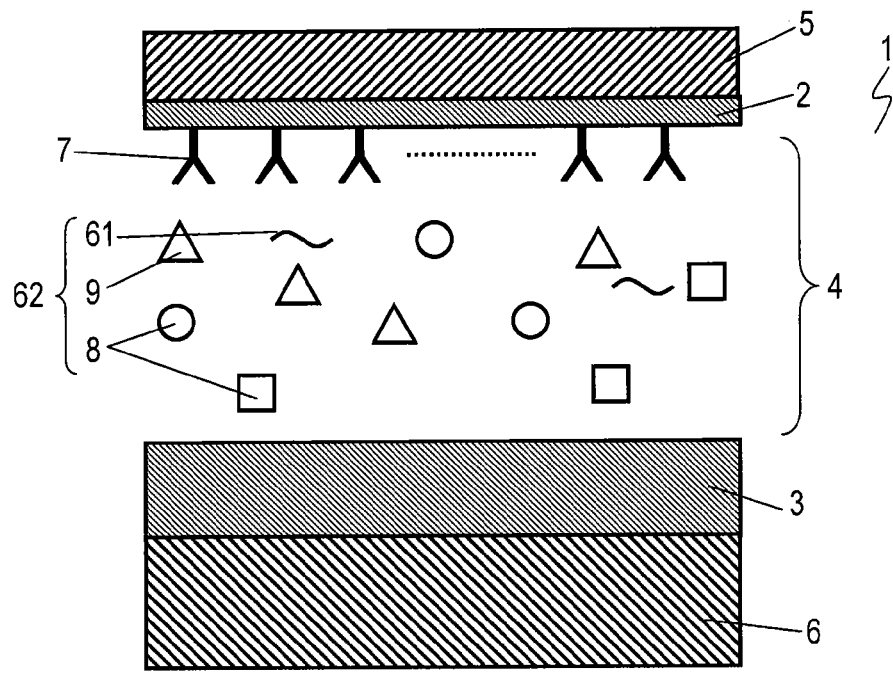
FIG. 3A is a cross-sectional view of the plasmon sensor according to Embodiment 1.
Figure 3B:
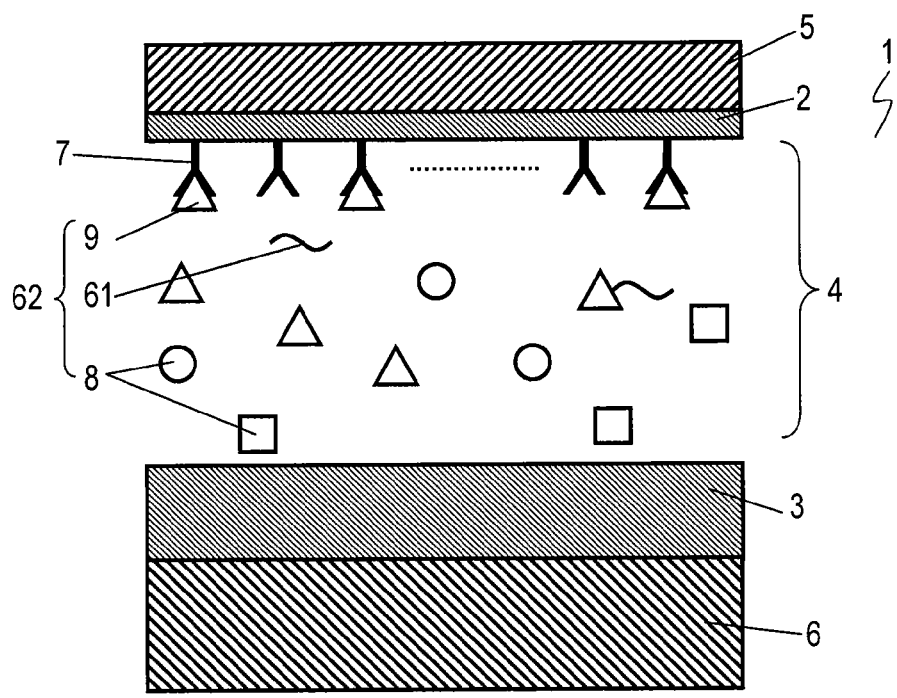
FIG. 3B is a cross-sectional view of the plasmon sensor according to Embodiment 1.

FIGS. 3A and 3B are cross-sectional views of plasmon sensor 1 for illustrating an operation of plasmon sensor 1. When test sample 62 containing non-specific analyte 9 and target analyte 8 is injected into hollow space 4 which is in vacuum or is filled with air, as shown in FIG. 3A, a state of hollow space 4, particularly the dielectric constant of hollow space 4, changes. This changes a resonance frequency that is a frequency generating the surface plasmon resonance in plasmon sensor 1.

Subsequently, when ligands 7 provided on lower surface 2B of metal layer 2 specifically bind with analyte 8, as shown in FIG. 3B, a thickness of organic substance and a relative dielectric constant around lower surface 2B of metal layer 2 changes, accordingly changing a dielectric constant of medium 61 as well as distribution of the dielectric constant between metal layers 2 and 3. As discussed, the resonance frequency of plasmon sensor 1 changes with the progress of the specific binding between ligands 7 and analyte 8. The change in the resonance frequency is observed to detect a state of the specific binding between ligands 7 and analyte 8, particularly strength of the specific binding, a speed and the like of the binding.

Figure 4A:
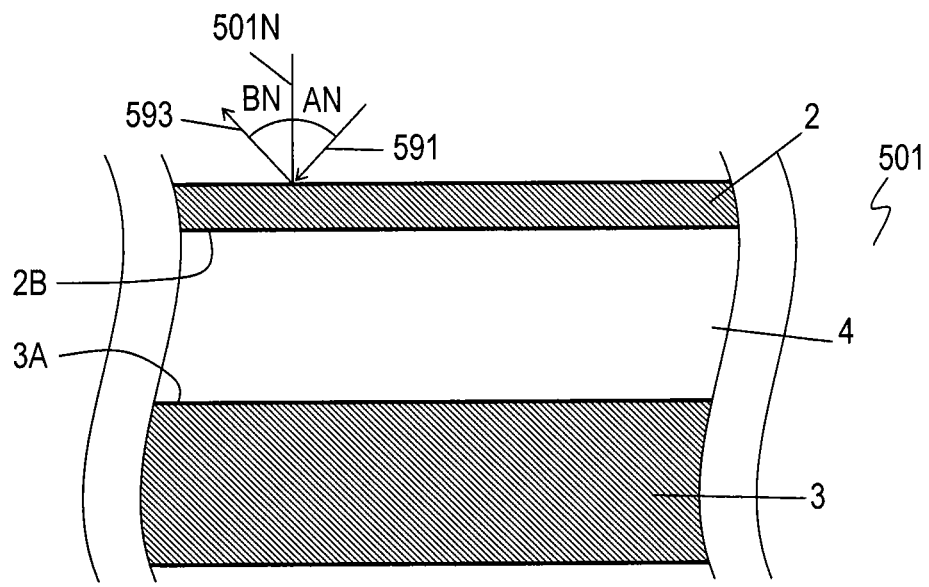
FIG. 4A is a schematic view of an analysis model of electromagnetic field simulation in the plasmon sensor according to Embodiment 1.
Figure 4B:
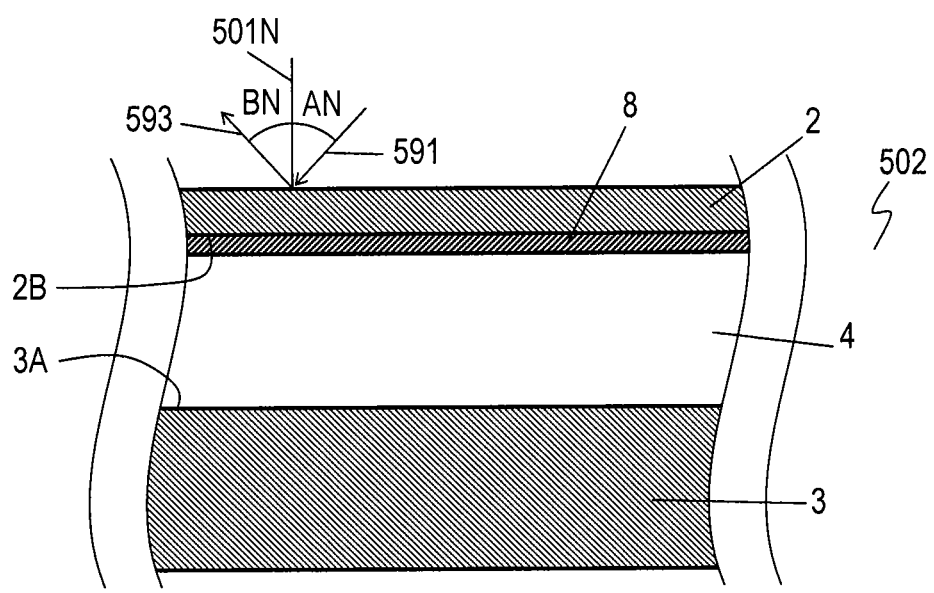
FIG. 4B is a schematic view of an analysis model of electromagnetic field simulation in the plasmon sensor according to Embodiment 1.

The change in the frequency of the surface plasmon resonance that occurs in plasmon sensor 1 due to specific binding between ligands 7 and analyte 8 will be described below with referring to electromagnetic field simulations. FIGS. 4A and 4B are schematic view of analysis models 501 and 502 for the electromagnetic field simulations of plasmon sensor 1, respectively.

In analysis model 501 shown in FIG. 4A, metal layer 2 is made of silver and has a thickness of 30 nm. Metal layer 3 is made of silver and has a thickness of 130 nm. The distance between metal layers 2 and 3 is 160 nm, and hollow space 4 is filled with air having a relative dielectric constant of 1.0. Both spaces above upper surface 2A of metal layer 2 and below lower surface 3B of metal layer 3 are filled with air. In analysis model 501, metal layers 2 and 3 and hollow space 4 extend infinitely.

Analysis model 502 shown in FIG. 4B is identical to analysis model 501 shown in FIG. 4A except that analyte 8 is provided on lower surface 2B of metal layer 2. Analyte 8 has a thickness of 10 nm, and has a relative dielectric constant of 3.0. The distance between analyte 8 and upper surface 3A of metal layer 3 is 150 nm, and hollow space 4 is filled with air having a relative dielectric constant of 1.0. Both spaces above upper surface 2A of metal layer 2 and below lower surface 3B of metal layer 3 are filled with the air. In analysis model 502, metal layers 2 and 3 and hollow space 4 extends infinitely.

A dielectric function of the silver to form metal layers 2 and 3 can be drawn by converting experimental data of refractive indices described in "Handbook of Optical Constants of Solids (Palik, Edward D. in 1998)". In analysis models 501 and 502 shown in FIGS. 4A and 4B, ligands 7 are not modeled to simplify the simulation analyses.

The electromagnetic field simulation analyses was conducted on analysis models 501 and 502 by sending electromagnetic wave 591 at descending angle AN of 45 degrees with respect to normal direction 501N perpendicular to upper surface 2A of metal layer 2, and by detecting electromagnetic wave 593 radiated from upper surface 2A of metal layer 2 at ascending angle BN of −45 degrees.

Figure 5:
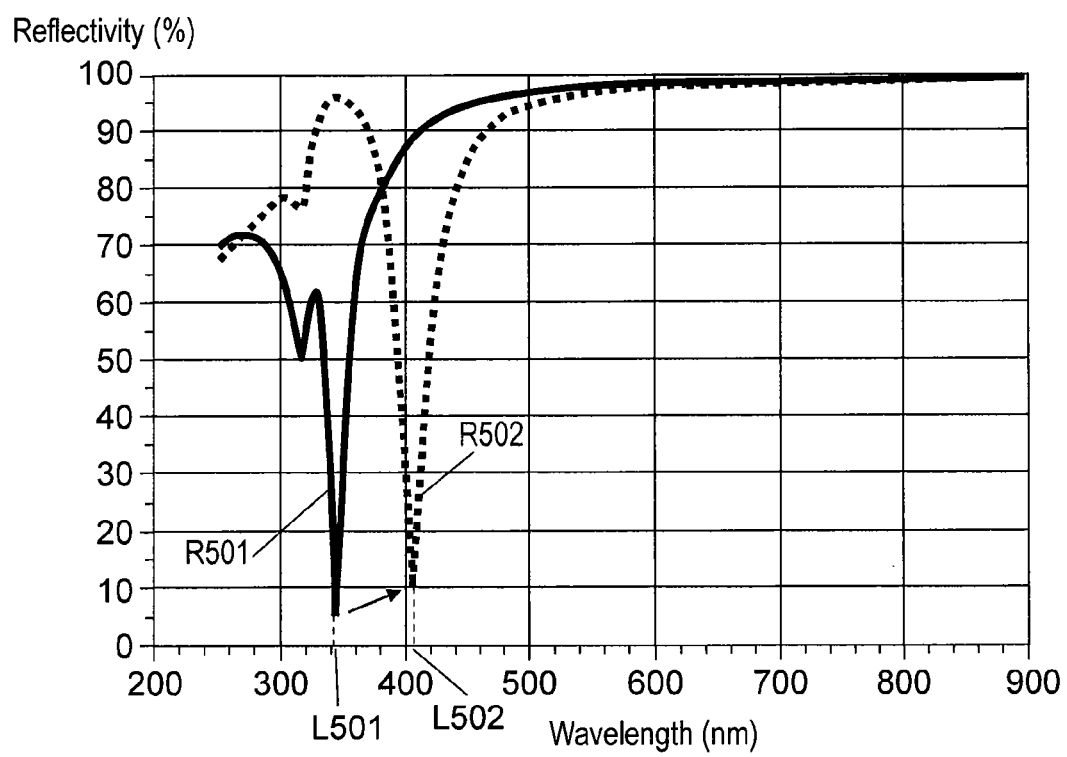
FIG. 5 shows an analysis result of the electromagnetic simulation of the plasmon sensor according to Embodiment 1.

FIG. 5 shows a result of the electromagnetic field simulation. In FIG. 5, the horizontal axis represents a wavelength of electromagnetic wave 591, and the vertical axis represents a reflectivity which is the ratio of power of electromagnetic wave 593 to power of electromagnetic wave 591. FIG. 5 shows reflectivities R501 and R502 of the respective analysis models 501 and 502.

As shown in FIG. 5, a value of reflectivity R501 decreases sharply locally near the wavelength of 340 nm of electromagnetic wave 591. Around resonant wavelength L501 of the electromagnetic wave at which the reflectivity becomes the smallest, the wave number of the electromagnetic wave supplied to hollow space 4 matches with the wave number of the surface plasmon generated on lower surface 2B of metal layer 2, and the surface plasmon resonance is hence excited on lower surface 2B of metal layer 2. Similarly, the surface plasmon resonance is excited on upper surface 3A of metal layer 3 since the wave number of electromagnetic wave 591 supplied to hollow space 4 matches with the wave number of the surface plasmon generated on upper surface 3A of metal layer 3 around resonant wavelength L501.

In analysis model 502 shown in FIG. 4B, resonant wavelength L502 at which a value of reflectivity R502 sharply and locally becomes the smallest is longer than resonant wavelength L501 of analysis model 501 by about 70 nm, as shown in FIG. 5. The value of the relative dielectric constant of analyte 8 added onto lower surface 2B of metal layer 2 of analysis model 502 shown in FIG. 4B changes to lower the resonance frequency for generating the surface plasmon resonance excited on lower surface 2B of metal layer 2, thereby resulting in the longer resonant wavelength by about 70 nm.

As noted, the result of the simulation analyses shown in FIG. 5 shows that the surface plasmon resonance is excited on lower surface 2B of metal layer 2. A change in the state of the medium around lower surface 2B of metal layer 2 is detectible by measuring a change in the resonance frequency (or resonant wavelength).

Plasmon sensor 1 detects not only the change in the resonance frequency but also a change in the reflectivity, and it can hence demonstrate a high detecting performance of the change in the state of the medium in the vicinity of lower surface 2B of metal layer 2 by using these two detected indices at the same time. The state of the medium in hollow space 4 means a state of the material filling partially or entirely inside hollow space 4, such as composition of the material and distribution of the material in hollow space 4.

In plasmon sensor 1, medium 61 can be either a gas or a liquid for test sample 62 containing analyte 8. However, gaseous test sample 62 containing medium 61 of a gaseous form can be injected easily into hollow space 4. Gaseous test sample 62 may be compressed when injected into hollow space 4, so that a density of analyte 8 in test sample 62 is increased to help expedite the specific binding between ligands 7 and analyte 8 and to increase the sensitivity of plasmon sensor 1.

Plasmon sensor 1 may be placed inside a storage compartment, such as a refrigerator, of food for use in controlling a condition of the food. For example, plasmon sensor 1 can be employed in a system that detects the rot of food automatically and notifies it to a responsible person. More specifically, electromagnetic wave source 92 including a light-emitting device, such as a light-emitting diode, is used to supply light, or electromagnetic wave 91, to metal layer 2 continuously or periodically from above upper surface 2A of metal layer 2 of plasmon sensor 1 disposed in the storage compartment. Detector unit 94 including a light-detecting device, such as a photodiode, detects light or electromagnetic wave 93 radiated from plasmon sensor 1, calculates and monitors the reflectivity. This system automatically notifies a user when a value of the reflectivity shifts to the outside of a predetermined range to let the user aware of a change in the state of the food without confirming it directly and periodically. The sensitivity of plasmon sensor 1 can also be increased in this instance by compressing the gas inside the storage compartment when injecting the gas into hollow space 4.

In addition, plasmon sensor 1 can be used as a sensor of lung cancer by having exhaled air of a patient injected into hollow space 4. Furthermore, plasmon sensor 1 can be used for monitoring indoor virus by installing it near an air intake opening of a humidifier, air cleaner, air conditioner or the like apparatus. In this instance, the intake air may be blown into a part of water stored for humidification or collected by dehumidification, and the air-contained water is then injected into hollow space 4 of plasmon sensor 1 to also use the advantage of the like effect. It is also feasible as another application to place plasmon sensor 1 in a water tub of a washing machine for the purpose of checking mold in the water tub.

In plasmon sensor 1 shown in FIG. 1, ligands 7 are provided on lower surface 2B of metal layer 2. Plasmon sensor 1 of Embodiment 1 does not necessarily include ligands 7 (77). Plasmon sensor 1 not provided with ligands 7 on any of lower surface 2B of metal layer 2 and upper surface 3A of metal layer 3 is still capable of detecting the presence or absence of any gas of detection target by injecting a sample gas into hollow space 4, and measuring any of a change in the resonance frequency, a change in the resonant wavelength and an absolute value of the resonance frequency. This structure can eliminate a process of forming ligands 7 (77) on the surfaces of metal layer 2 or 3, and improve the manufacturing efficiency of the plasmon sensor.

Another alternative is to dispose a substance having a property of chemically reacting with the gas of detection target on lower surface 2B of metal layer 2 or upper surface 3A of metal layer 3, instead of ligands 7 (77). A plasmon sensor of this structure can detect the chemical reaction on lower surface 2B of metal layer 2 or upper surface 3A of metal layer 3 by monitoring any of the change in the resonance frequency and the change in the resonant wavelength.

Figure 6:
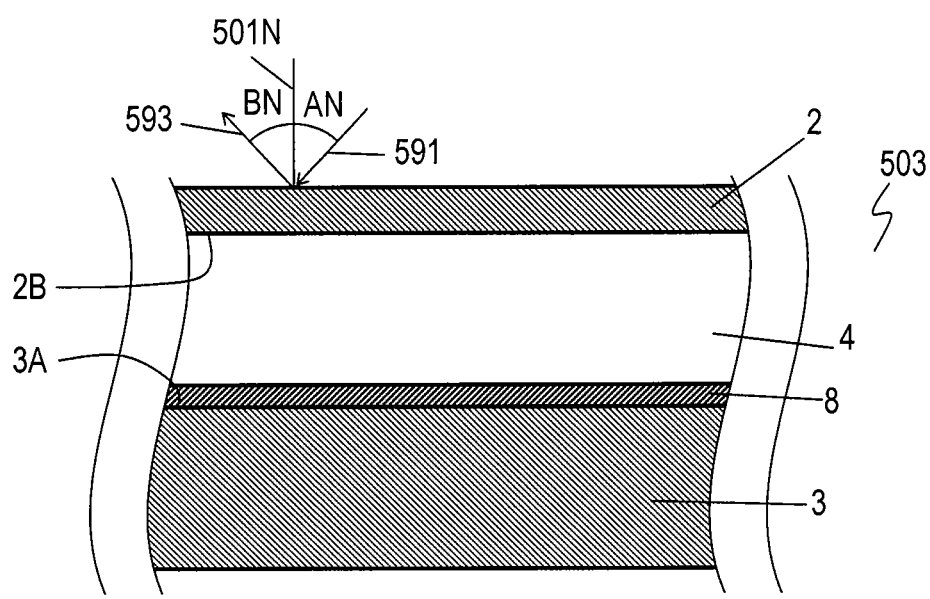
FIG. 6 is a schematic view of an analysis model of electromagnetic field simulation in the plasmon sensor according to Embodiment 1.

FIG. 6 is a schematic view of another electromagnetic simulation model 503 of plasmon sensor 1. In FIG. 6, components identical to those of analysis models 501 and 502 shown in FIGS. 4A and 4B are denoted by the same reference numerals. Model 503 does not include with ligands 7 on lower surface 2B of metal layer 2, but includes ligands 77 disposed on upper surface 3A of metal layer 3.

In analysis model 503 shown in FIG. 6, analyte 8 disposed on upper surface 3A of metal layer 3 has a thickness of 10 nm and a relative dielectric constant of 3.0. A spatial thickness of hollow space 4 is 150 nm, and this space has a relative dielectric constant of 1.0.

The electromagnetic field simulation analysis was conducted on analysis model 503 by sending electromagnetic wave 591 at a descending angle AN of 45 degrees with respect to the normal direction 501N perpendicular to upper surface 2A of metal layer 2, and detecting electromagnetic wave 593 radiated from upper surface 2A of metal layer 2 at an ascending angle of −45 degrees.

Figure 7:
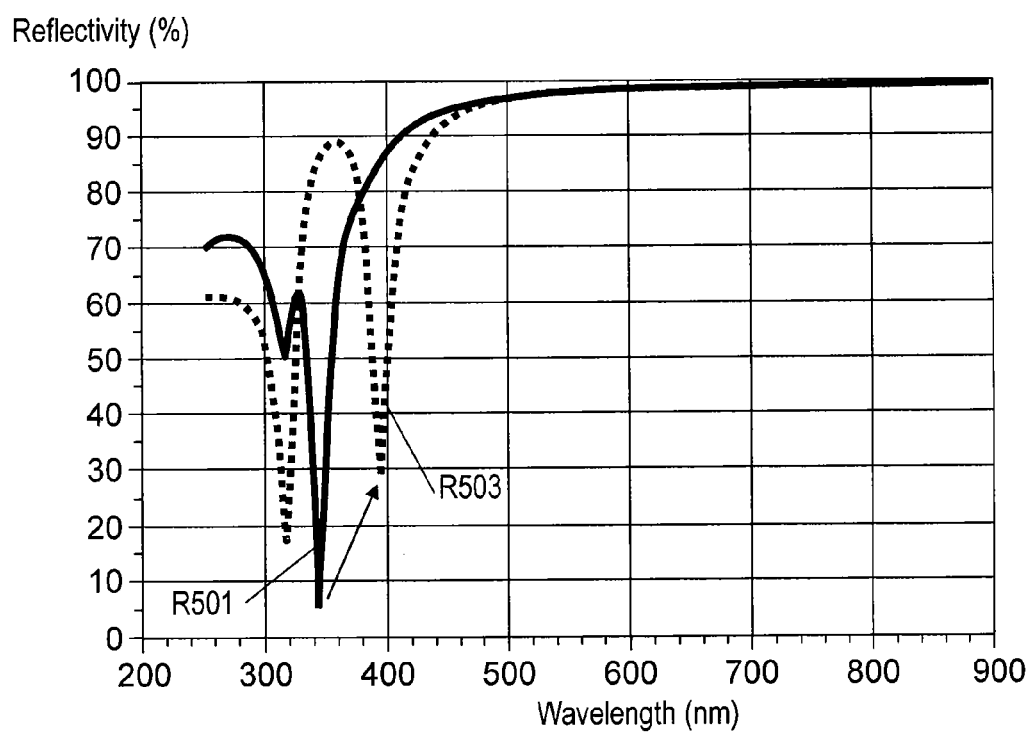
FIG. 7 shows an analysis result of the simulation of the plasmon sensor according to Embodiment 1.

FIG. 7 shows analysis results of the electromagnetic field simulations made on analysis models 501 and 503 shown in FIGS. 4A and 6. In FIG. 7, the horizontal axis represents the wavelength of electromagnetic wave 591, and the vertical axis represents a reflectivity which is the ratio of power of electromagnetic wave 593 to power of electromagnetic wave 591. FIG. 7 shows reflectivities R501 and R503 of the respective analysis models 501 and 503, respectively.

As shown in FIG. 7, a change in the resonant wavelength is observed even when analyte 8 is placed on upper surface 3A of metal layer 3. This indicates that surface plasmon resonance is generated on upper surface 3A of metal layer 3. In other words, it is adequate to place ligands 77 on upper surface 3A of metal layer 3 without placing ligands 7 on lower surface 2B of metal layer 2, and this can improve flexibility in designing plasmon sensor 1.

Plasmon sensor 1 may include ligands 7 placed on lower surface 2B of metal layer 2 and ligands 77 placed on upper surface 3A of metal layer 3. Plasmon sensor 1 having such a structure provides advantage of the surface plasmon resonance occurring on both of lower surface 2B of metal layer 2 and upper surface 3A of metal layer 3, thereby providing plasmon sensor 1 with a high sensitivity.

Figure 8:
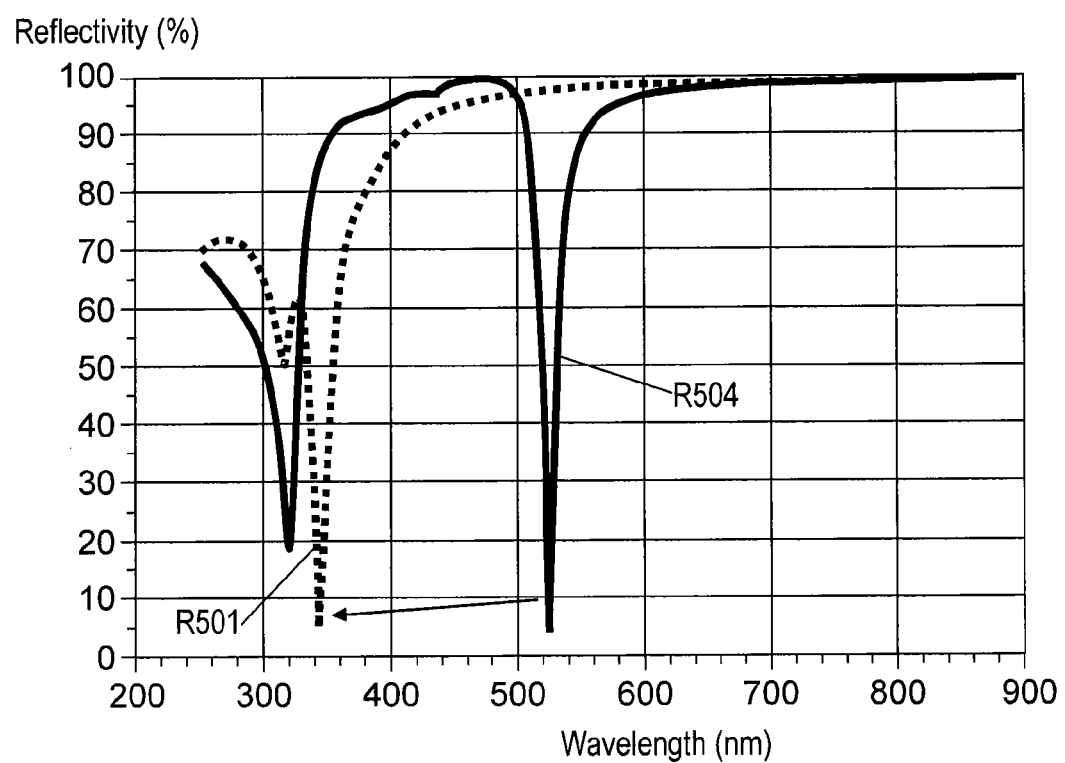
FIG. 8 shows an analysis result of another simulation of the plasmon sensor according to Embodiment 1.

FIG. 8 shows analysis results made on analysis model 501 shown in FIG. 4A and another analysis model 503 of the same configuration as model 501 except for hollow space 4 having a relative dielectric constant of 2.0. In FIG. 8, the horizontal axis represents the wavelength of electromagnetic wave 591, and the vertical axis represents the reflectivity which is the ratio of power of electromagnetic wave 593 to power of electromagnetic wave 591. Analysis model 504 exhibits reflectivity R504.

As shown in FIGS. 5, 7 and 8, surface plasmon resonance occurs even when hollow space 4 is in vacuum or filled with air, that is, even if hollow space 4 is not filled with a dielectric substance of a solid form having a high dielectric constant.

In plasmon sensor 1, hollow space 4 formed between metal layers 2 and 3 is not filled with a solid dielectric substance. This structure allows test sample 62 containing analyte 8 to be injected into hollow space 4 to allows analyte 8 to contact ligands 7 (77).

Medium 61 of the air or vacuum in hollow space 4 to have a small relative dielectric constant can shorten the resonant wavelength of the surface plasmon resonance, as shown in FIG. 8. In other words, The spatial distance between metal layers 2 and 3 for sensor 1 having hollow space 4 filled with the air or in vacuum can be larger than the spatial distance of a hollow space of a plasmon sensor filled with any dielectric substance to obtain the same resonance frequency.

Hollow space 4 is in vacuum or filled with air having the relative dielectric constant of about 1.0 or any other gas having a small relative dielectric constant like plasmon sensor 1 of the present application. This structure can increase the spatial distance between metal layers 2 and 3 compared to other plasmon sensors filled with a solid dielectric substance between metal layers 2 and 3. This structure can increase the spatial thickness of hollow space 4, allowing test sample 62 containing analyte 8 to be injected into hollow space 4.

Figure 9A:
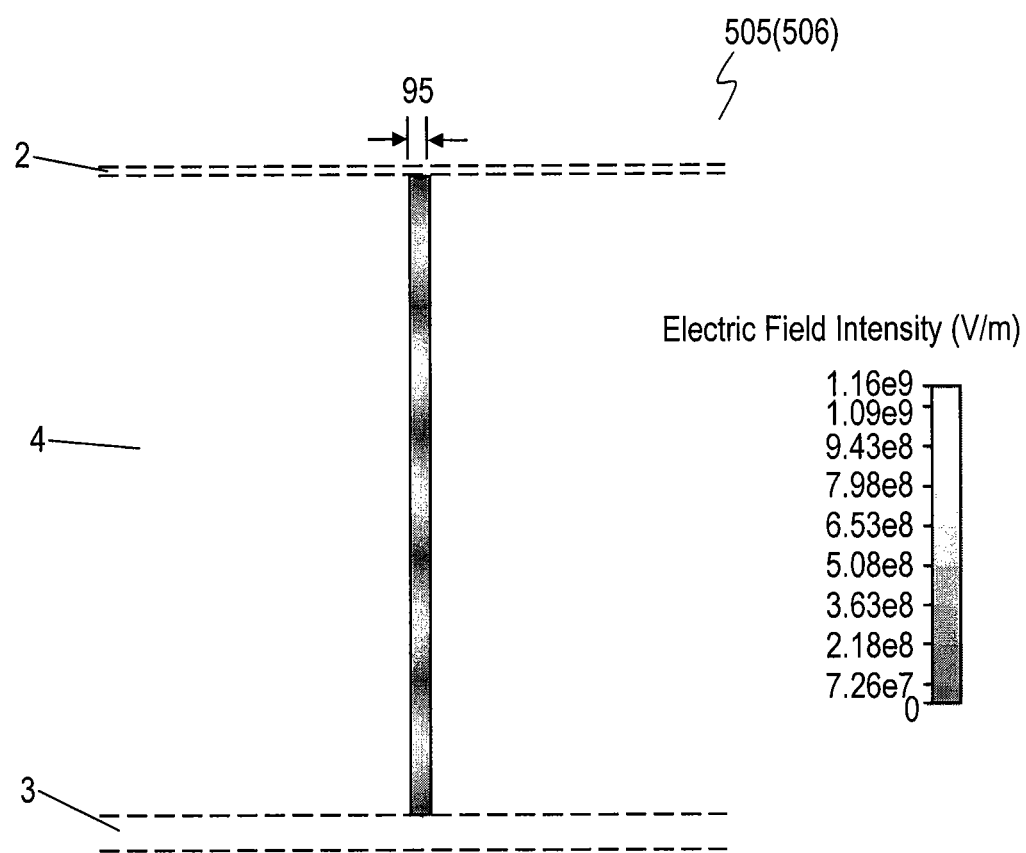
FIG. 9A shows an analysis result of another simulation of the plasmon sensor according to Embodiment 1.
Figure 9B:
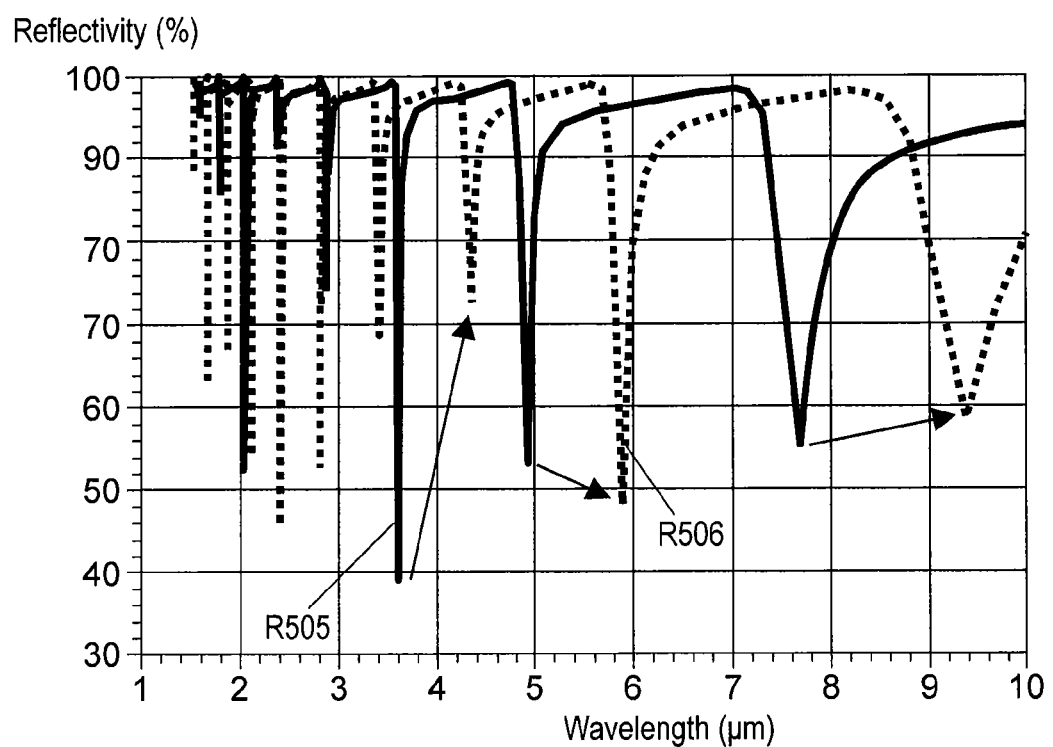
FIG. 9B shows an analysis result of another simulation of the plasmon sensor according to Embodiment 1.

Additionally, the electromagnetic field intensity can be distributed in a high-order mode between metal layers 2 and 3 at the resonance frequency. That is, the electromagnetic field generated between metal layers 2 and 3 may have a high intensity at plural positions. FIGS. 9A and 9B show results of the electromagnetic field simulation performed on analysis model 505 having the same configuration as analysis model 501 shown in FIG. 4A except for hollow space 4 of 10 μm in the spatial thickness.

The model shown in FIG. 9A has a resonant wavelength of 2,883 nm. FIG. 9A shows distribution of the electric field intensity in hollow space 4. FIG. 9A shows the distribution of the electric field in partial area 95 rather than the entire area of hollow space 4 to simplify the explanation.

In FIG. 9A, the electric field intensity between metal layers 2 and 3 regularly repeats a local variation along the direction from metal layer 2 toward metal layer 3. The electric field intensity is small in the areas near metal layers 2 and 3. In FIG. 9A, the electric field having high intensity locally at plural positions, i.e., five areas, between metal layers 2 and 3, thus indicating the distribution of the electromagnetic field intensity in a high-order mode higher than the primary mode.

The electromagnetic field intensity distributed in the high-order mode between metal layers 2 and 3 provides an advantage of increasing the spatial distance between metal layers 2 and 3 to allow test sample 62 containing analyte 8 to be injected into hollow space 4 easily.

In analysis model 505 shown in FIG. 9A, hollow space 4 has a relative dielectric constant of 1.0. FIG. 9B shows reflectivities R505 and R506 representing results of the electromagnetic field simulation performed on analysis model 505 and analysis model 506 having the same configuration as analysis model 505 except for the hollow space having a relative dielectric constant of 1.2.

As shown in FIG. 9B, the surface plasmon resonance is generated in various resonant wavelengths in both of analysis models 505 and 506. In addition, the resonant wavelength changes when a state of medium, or the relative dielectric constant in hollow space 4 is changed.

If hollow space 4 has a large thickness, a high-order mode of the electromagnetic field intensity distribution occurs between metal layers 2 and 3, and surface plasmon resonance of a high-order frequency is generated.

Plasmon sensor 1 also has a function of detecting a temporal variation in the state of medium 61 inside hollow space 4 by using the surface plasmon resonance generated in the frequency of high-order mode. This provides the advantage of increasing the spatial distance between metal layers 2 and 3, and allows test sample 62 containing analyte 8 to be injected easily into hollow space 4.

A method of deriving an order of the high-order mode in plasmon sensor 1 will be described below.

Electromagnetic field intensity is distributed in an m-th order mode between metal layers 2 and 3 before test sample 62 which has a refractive index n and which does not contain analyte 8 is injected into hollow space 4. Equation 1 is provided where a is an integer not smaller than 1.

$$(1/2) \times \lambda \times m = (1/2) \times (\lambda/n) \times (m+a) \qquad \text{(Equation 1)}$$

In Equation 1, λ is a wavelength of electromagnetic wave 91 supplied into hollow space 4 from above upper surface 2A of metal layer 2 before medium 61 is disposed in hollow space 4.

The left side of Equation 1 represents a distance between metal layers 2 and 3 before medium 61 is disposed in hollow space 4. In other words, the distance between metal layers 2 and 3 is given by the formula in the left side of Equation 1 since the electromagnetic field intensity distribution of an m-th order mode is produced between metal layers 2 and 3 before medium 61 is disposed in hollow space 4.

The right side of Equation 1 represents a distance between metal layers 2 and 3 after medium 61 is disposed in hollow space 4. In other words, the wavelength λ of electromagnetic wave 91 inside hollow space 4 is shortened to 1/n when medium 61 having refractive index n is disposed in hollow space 4. This produces more nodes and antinodes of the electromagnetic field intensity between metal layers 2 and 3 than before medium 61 is disposed. If the electromagnetic field intensity distribution in this condition is a (m+a)-th order mode, a distance between metal layers 2 and 3 is expressed by the right side of Equation 1. The left and right sides of Equation 1 are equal to each other since these sides represent the distance between metal layers 2 and 3. Integer a denotes the difference in the order of the distribution mode of the electromagnetic field intensity that changes between the presence and absence of medium 61 (i.e., test sample 62 not containing analyte 8) between metal layers 2 and 3.

According to Equation 1, the order m of the high-order mode, refractive index n, and integer a satisfy Equation 2.

$$m = a/(n-1) \quad \text{(Equation 2)}$$

The change in the resonant wavelength of plasmon sensor 1 is detectible visibly by the user. That is, the change in the resonant wavelength can be detected according to color of the reflected light from plasmon sensor 1. In order to determine whether test sample 62 contains analyte 8 or not, it is necessary that the color of the reflected light from plasmon sensor 1 changes only when test sample 62 containing analyte 8 is disposed in hollow space 4 whereas the color of the reflected light does not change when test sample 62 containing only medium 61 is disposed in hollow space 4. In other words, it is necessary to prevent the color of the reflected light from plasmon sensor 1 from changing due simply to test sample 62, disposed into hollow space 4, which contains not analyte 8 but only medium 61.

In the case of using test sample 62 containing medium 61 of water but no analyte 8, for instance, the order m is obtained as follows. The refractive index n of the water is 1.3334. Integer a is set to 1, the order m is determined by the following according to the Equation 2.

$$m = 2.9994 \approx 3$$

The visible light range is a range of wavelength of the light that is visible by human eyes, and is a range between 380 nm and 750 nm. Plasmon sensor 1 is designed to produce surface plasmon resonance at frequency fb of blue color within a wavelength range between 450 nm and 495 nm, for example, which is within the visible light range.

The distance between metal layers 2 and 3 is determined so that electromagnetic field distribution of the third-order mode (this is because m≈3 is derived as a result of the above calculation) is produced in hollow space 4 at the frequency fb under the state of hollow space 4 not filled with water but only with air. Plasmon sensor 1 generates surface plasmon resonance at about frequency fb. When white light having the entire frequency components of the visible light range enters upper surface 2A of metal layer 2, blue light is selectively attenuated in the incident white light when the light is reflected on upper surface 2A and radiated upward. Next, when test sample 62 containing medium 61 of water but no analyte is put into hollow space 4, electromagnetic field distribution of generally the fourth-order mode (m+a=2.9994+1≈4) is generated at the frequency fb between metal layers 2 and 3. In other words, the color of the light reflected upward from metal layer 2 does not change substantially since plasmon sensor 1 produces the surface plasmon resonance at the frequency fb even when test sample 62 (medium 61) not containing analyte 8 is put into hollow space 4. Hence, the resonant wavelength of plasmon sensor 1 does not shift substantially due only to whether or not test sample 62 placed in hollow space 4 contain no analyte 8 but only medium 61.

In the above condition, integer m used is an integral value obtained by rounding off the value of m derived from the calculation since the value rarely becomes an integral number although the value m is close to 3.

The distance between metal layers 2 and 3 can be designed such that the wavelength of generating the surface plasmon resonance changes only within a predetermined wavelength range out of wavelength range A (between 380 nm and 450 nm), wavelength range B (between 450 nm and 495 nm), wavelength range C (between 495 nm and 570 nm), wavelength range D (between 570 nm and 590 nm), wavelength range E (between 590 nm and 620 nm) and wavelength range F (between 620 nm and 750 nm), when the state of hollow space 4 is changed from the state that hollow space is not filled with test sample 62, or medium 61 not containing analyte 8, to the state that hollow space 4 is filled only with medium 61. To be more specific, the order of the distribution mode of the electromagnetic field produced between metal layers 2 and 3 is determined as described above.

Wavelength range A (between 380 nm and 450 nm) corresponds to color of violet of visible light. Wavelength range B (between 450 nm and 495 nm) corresponds to color of blue of visible light. Wavelength range C (between 495 nm and 570 nm) corresponds to color of green of visible light. Wavelength range D (between 570 nm and 590 nm) corresponds to color of yellow of visible light. Wavelength range E (between 590 nm and 620 nm) corresponds to color of orange of visible light. Wavelength range F (between 620 nm and 750 nm) corresponds to color of red of visible light. The change in the wavelength of the reflected light is limited within one wavelength range out of the above ranges to prevent a substantial change in color of the reflected light from plasmon sensor 1 due to the presence and absence of test sample 62 not containing analyte 8, thereby avoiding confusion to the user. Thus, plasmon sensor 1 enables human to simply and visually detect only the presence or absence of analyte 8 and antigen-antibody reaction.

Hollow space 4 may occupy substantially the entire area (including an area where ligands 7 are not formed) between metal layers 2 and 3. Alternatively, hollow space 4 may be provided in an area other than an area where a post or a wall for supporting metal layers 2 and 3 are not provided (including the area where ligands 7 are not formed) between metal layers 2 and 3. In addition, a coating layer for protection against corrosion on each of lower surface 2B and upper surface 3A of metal layers 2 and 3. In this case, hollow space 4 can be provided in an area other than the coating layer for corrosion protection between metal layers 2 and 3 (excluding the area occupied by ligands 7 formed on surfaces of metal layers 2 and 3 not covered with the coating). Hollow space 4 is a space where test sample 62 can be injected. Hollow space 4 exists in a part of the area between metal layers 2 and 3.

When surface plasmon resonance occurs at frequency F, spatial distance L between metal layers 2 and 3 is expressed by Equation 3:

$$L = N \times C/(2 \times F) \times \cos\theta \quad \text{(Equation 3)}$$

N is an integer larger than zero, or N>0, C is an effective speed of light between metal layers 2 and 3, and θ is an incidence angle of the electromagnetic wave in hollow space 4 with respect to the normal line perpendicular to surfaces 2B and 3A of metal layers 2 and 3.

Equation 3 does not take into account complex refractive indices of metal layers 2 and 3, hence containing an error. If a media (e.g., a post, wall, and the like mentioned above) other than hollow space 4 is located between metal layers 2 and 3, the value of C in Equation 3 is determined in consideration of the media.

The electromagnetic wave that passes thorough metal layer 2 and enters hollow space 4 is reflected by upper surface 3A of metal layer 3, and produces a standing distribution of the intensity of the electromagnetic field, as shown in FIG. 9A. A part of the standing electromagnetic field distributed in hollow space 4 is used as an energy source to generate the surface plasmon resonance.

Plasmon sensor 1 may be so designed such that the resonant wavelength changes from a wavelength range of invisible light outside of a visible light range to the inside of the visible light range or from the visible light range to an invisible light range by changing the state of medium 61 in hollow space 4 with time.

For instance, when the resonant wavelength is changed from the invisible light range to the visible light range due to a change in the state of medium inside hollow space 4 by a specific binding between ligand 7 and analyte 8, the surface plasmon resonance causes a part of colors in the visible light range that is detectible by human eye not to be reflected or radiated from plasmon sensor 1. As a result, the specific binding between ligands 7 and analyte 8 can be detected with the human eye, thus providing simple plasmon sensor 1 not equipped with a complex and large-scale instrument.

In the configuration discussed above, the electromagnetic wave supplied to plasmon sensor 1 includes at least a part of wavelengths in the visible light range. Specifically, it is conceivable to have a configuration that applies white light of the sunlight or light of a lighting unit to plasmon sensor 1, and detects a reflected or radiated wave of the light with human vision. This allows the specific binding and the like of ligands 7 and analyte 8 to be detected easily with human eye.

The resonant wavelength changed when an irradiation angle of the electromagnetic wave to plasmon sensor 1 (i.e., an incidence angle of the electromagnetic wave to metal layer 2) changes. Therefore, plasmon sensor 1 may be designed to have a characteristic that the resonant wavelength remains within a range of the invisible light range or within a range of wavelengths having the same color in the visible light range even when the irradiation angle of the electromagnetic wave to plasmon sensor 1 is changed within a possible range just before the specific binding occurs, while holding plasmon sensor 1 with a hand to cause the sunlight to enter to metal layer 2 and detecting the specific binding between ligands 7 and analyte 8. This configuration prevents plasmon sensor 1 from changing the color of reflected light even when the irradiation angle of the electromagnetic wave to plasmon sensor 1 is changed within the possible range. Materials of supporters 5 and 6, thicknesses and materials of metal layers 2 and 3, the distance between metal layers 2 and 3 are factors to be adjusted in order to design plasmon sensor 1 with the characteristic to maintain the resonant wavelength within the range of the invisible light range or within the range of wavelengths having same color in the visible light range even when the irradiation angle of the electromagnetic wave to plasmon sensor 1 is changed within the possible range under the state before the specific binding occurs.

In the configuration discussed above, the resonant wavelength of plasmon sensor 1 is changed from the invisible light range to the visible light range or from the visible light range to the invisible light range. Conventional plasmon sensor 100 shown in FIG. 28 may also be designed to cause this change. To be more specific, conventional plasmon sensor 100 provided with prism 101 shown in FIG. 28 can be configured such that the resonant wavelength changes either from the invisible light range to the visible light range or from the visible light range to the invisible light range before and after the specific binding between ligands and analyte. The same idea can be applied to a sensor that uses localization plasmon. This can make possible detection of the specific binding and the like between the ligand and the analyte easily with the human eye.

Furthermore, plasmon sensor 1 of the present invention can also be so designed that the wavelength of generating the surface plasmon resonance changes from the invisible light range to one of a range between 450 nm and 570 nm and a range between 620 nm and 750 nm, or changes to the invisible light range from one of the range between 450 nm and 570 nm and the range between 620 nm and 750 nm by changing the state of medium 61 in hollow space 4 with time.

Here, the electromagnetic wave of the wavelength between 450 nm and 570 nm corresponds to a range of blue light (between 450 nm and 495 nm) and green light (between 495 nm and 570 nm). The electromagnetic wave of the wavelength between 620 nm and 750 nm corresponds to red light.

The pyramidal cells densely distributed in the center of the human retina consist of three different kinds of pyramids; pyramids which absorb red light; pyramids which absorb green light; and pyramids which absorb blue light. This causes a human to sense only three colors of light, red, blue and green.

Using red, blue and green lights that are highly sensitive for the human eye, the plasmon sensor can detect the binding easily with the human vision.

When the resonant wavelength changes from the invisible light range to one of the range between 450 nm and 750 nm and the range between 570 nm and 620 nm due to a change in the state of the medium inside hollow space 4 attributed to the specific binding between ligands 7 and analyte 8, for instance, the surface plasmon resonance causes the light of one color among blue, green and red that are highly sensitive for the human eye not to be reflected or radiated from plasmon sensor 1. As a result, it makes possible the detection of specific binding between ligands 7 and analyte 8 with the human eye.

It is also true in this case that the resonant wavelength varies when an irradiation angle of the electromagnetic wave to plasmon sensor 1 (i.e., the incidence angle of the electromagnetic wave to metal layer 2) changes. Therefore, plasmon sensor 1 may be so designed that it has a characteristic that the resonant wavelength remains inside the range of the invisible light range or inside the range of wavelengths having the same color in the visible light range even when the irradiation angle of the electromagnetic wave to plasmon sensor 1 is changed within a possible range under the state just before the specific binding occurs, while holding plasmon sensor 1 with a hand to let the sunlight enter the face side of metal layer 2 and detecting the specific binding between ligands 7 and analyte 8. It is by virtue of this configuration that achieves plasmon sensor 1 capable of avoiding the color of reflected light from changing even when the irradiation angle of the electromagnetic wave to plasmon sensor 1 is varied within the possible range.

In the case discussed above, the electromagnetic wave applied to plasmon sensor 1 includes at least the wavelengths of blue, green and red lights. It is for this reason that the specific binding and the like between ligands 7 and analyte 8 are detectible with the human eye as mentioned above.

In the above embodiment, the resonant wavelength of plasmon sensor 1 is changed from the invisible light range to one of the range between 450 nm and 570 nm and the range between 620 nm and 750 nm, or from one of the range between 450 nm and 570 nm and the range between 620 nm and 750 nm to the invisible light range. The change of this kind may also be applied to conventional plasmon sensor 100. To be more specific, conventional plasmon sensor 100 provided with prism 101 shown in FIG. 28 can be configured so that the resonant wavelength is changed either from the invisible light range to one of the range between 450 nm and 570 nm and the range between 620 nm and 750 nm, or from one of the range between 450 nm and 570 nm and the range between 620 nm and 750 nm to the invisible light range before and after the specific binding between ligands and analyte. The same change can be applied to a sensor that uses localization plasmon. This can make possible to easily detect the specific binding and the like between the ligand and the analyte with the human eye.

Furthermore, plasmon sensor 1 can be designed such that the wavelength of generating the surface plasmon resonance changes from the range between 450 nm and 570 nm to another range between 495 nm and 580 nm by changing the state of medium 61 in hollow space 4 with time.

The electromagnetic wave in the range of wavelength between 450 nm and 495 nm corresponds to blue light in the range of visible light (i.e., the light of the wavelength visible by the human eye), and the electromagnetic wave in the range between 495 nm and 570 nm corresponds to green light in the range of visible light.

In one typical example, light reflected or radiated from plasmon sensor 1 is detected by the human eye while the sunlight or illumination light containing a wide range of visible rays is irradiated to plasmon sensor 1 from above upper surface 2A of metal layer 2. Since plasmon sensor 1 produces the surface plasmon resonance in the wavelength between 450 nm and 495 nm corresponding to blue light before the medium inside hollow space 4 changes, plasmon sensor 1 reflects or radiates the electromagnetic wave (light) with only the blue light corresponding to the resonant wavelength attenuated out of the sunlight or the illumination light containing the wide range of visible rays. Hence a person visually detects the electromagnetic wave (light) of such feature.

After the medium inside hollow space 4 changes, plasmon sensor 1 produces the surface plasmon resonance in the wavelength between 495 nm and 580 nm corresponding to green light. Plasmon sensor 1 thus reflects or radiates the electromagnetic wave (light) with only the green light corresponding to the resonant wavelength attenuated out of the sunlight or the illumination light containing the wide range of visible rays. A person visually detects the electromagnetic wave (light) of such feature. As the human eyes have high sensitivity to the blue and green lights, it is easy for anyone to detect the change in the resonant wavelength from the blue light range to the green light range as a result of the change of the medium inside hollow space 4. Accordingly, the plasmon sensor provides detection only with the human vision without using another device, such as a photo detector.

Although the above example illustrates the sunlight and illumination light as the source of electromagnetic wave, this is illustrative and not restrictive such that any source may be used as long as it includes at least blue and green lights.

It is also possible to reduce an extent of variation in the resonant wavelength attributed to a change of the medium inside hollow space 4 since the wavelength ranges of the blue and green lights used in the above example adjoin each other, thereby achieving the plasmon sensor useful for such analyte 8 having a low relative dielectric constant.

Plasmon sensor 1 of the present invention is illustrated as an example having the resonant wavelength changed from the range between 450 nm and 495 nm to another range between 495 nm and 580 nm. This design idea is applicable not only to plasmon sensor 1 of the present invention, but to conventional plasmon sensor 100. To be more specific, conventional plasmon sensor 100 provided with prism 101 shown in FIG. 28 can be designed such that the resonant wavelength is changed from the range between 450 nm and 495 nm to another range between 495 nm and 580 nm before and after the specific binding between ligands and analyte. The same change can be applied also to the sensor that uses localization plasmon. This can make possible to easily detect the specific binding and the like between ligands and analyte with the human eye.

Plasmon sensor 1 of the present invention can be designed (the design specifically including, e.g. a distance between metal layers 2 and 3, a thickness of metal layer 2 of plasmon sensor 1) such that the wavelength of generating the surface plasmon resonance changes from one wavelength range out of wavelength range A (between 380 nm and 450 nm), wavelength range B (between 450 nm and 495 nm), wavelength range C (between 495 nm and 570 nm), wavelength range D (between 570 nm and 590 nm), wavelength range E (between 590 nm and 620 nm) and wavelength range F (between 620 nm and 750 nm) to another range out of ranges A to F, when the state of medium 61 inside hollow space 4 is changed with time. A specific binding between ligands and analyte can be detected simply with the human eye when a change occurs in a state of the medium inside hollow space 4 with time (i.e., when the specific binding occurs between the ligands and the analyte in hollow space 4) since the resonant wavelength in one of the wavelength ranges A to F before the specific binding shifts to another range after the specific binding.

As stated above, plasmon sensor 1 of the present invention is designed to have the resonance wavelength changed from one wavelength range out of wavelength range A (between 380 nm and 450 nm), wavelength range B (between 450 nm and 495 nm), wavelength range C (between 495 nm and 570 nm), wavelength range D (between 570 nm and 590 nm), wavelength range E (between 590 nm and 620 nm) and wavelength range F (between 620 nm and 750 nm) to another range out of ranges A to F. This change may be applied to conventional plasmon sensor 100. To be more specific, conventional plasmon sensor 100 provided with prism 101 shown in FIG. 28 can be designed such that the resonant wavelength is changed from one wavelength range out of wavelength range A (between 380 nm and 450 nm), wavelength range B (between 450 nm and 495 nm), wavelength range C (between 495 nm and 570 nm), wavelength range D (between 570 nm and 590 nm), wavelength range E (between 590 nm and 620 nm) and wavelength range F (between 620 nm and 750 nm) to another range out of ranges A to F before and after the specific binding between ligands and analyte. The same change can be applied also to the sensor that uses localization plasmon. This can make possible to easily detect the specific binding and the like between ligands and analyte with the human eye.

Furthermore, the plasmon sensor may be designed such that the wavelength of generating the surface plasmon resonance changes from the invisible light range to one of wavelength range A (between 380 nm and 450 nm), wavelength range B (between 450 nm and 495 nm), wavelength range C (between 495 nm and 570 nm), wavelength range D (between 570 nm and 590 nm), wavelength range E (between 590 nm and 620 nm) and wavelength range F (between 620 nm and 750 nm), or from one of the wavelength ranges A, B, C, D, E, and F to the invisible light range by changing the state of medium 61 in hollow space 4 with time. When the state of medium 61 inside hollow space 4 changes with time (i.e., when the specific binding occurs between ligands and analyte in hollow space 4), reflected light having a wavelength in one of the wavelength ranges A, B, C, D, E, and F (i.e., the light reflected from plasmon sensor 1) is attenuated due to the surface plasmon resonance in the state of at least before or after the change takes place. The specific binding between ligands and analyte can be detected simply with the human eye.

In the case stated above, plasmon sensor 1 is designed to have the resonance wavelength changed from the invisible light range to one of the wavelength ranges A, B, C, D, E and F, or from one of the wavelength ranges A, B, C, D, E and F to the invisible light range. This design idea is applicable not only to plasmon sensor 1, but to conventional plasmon sensor 100. To be more specific, conventional plasmon sensor 100 provided with prism 101 shown in FIG. 28 can be designed such that the resonant wavelength is changed from the invisible light range to one of the wavelength ranges A, B, C, D, E and F, or from one of the wavelength ranges A, B, C, D, E and F to the invisible light range before and after the specific binding between ligands and analyte. The same idea can be applied to a plasmon sensor that uses localization plasmon so as to cause a change in the wavelength of reflected light from the sensor. This allows the specific binding between ligands 7 and analyte 8 to be detected easily with the human eye.

Figure 28:
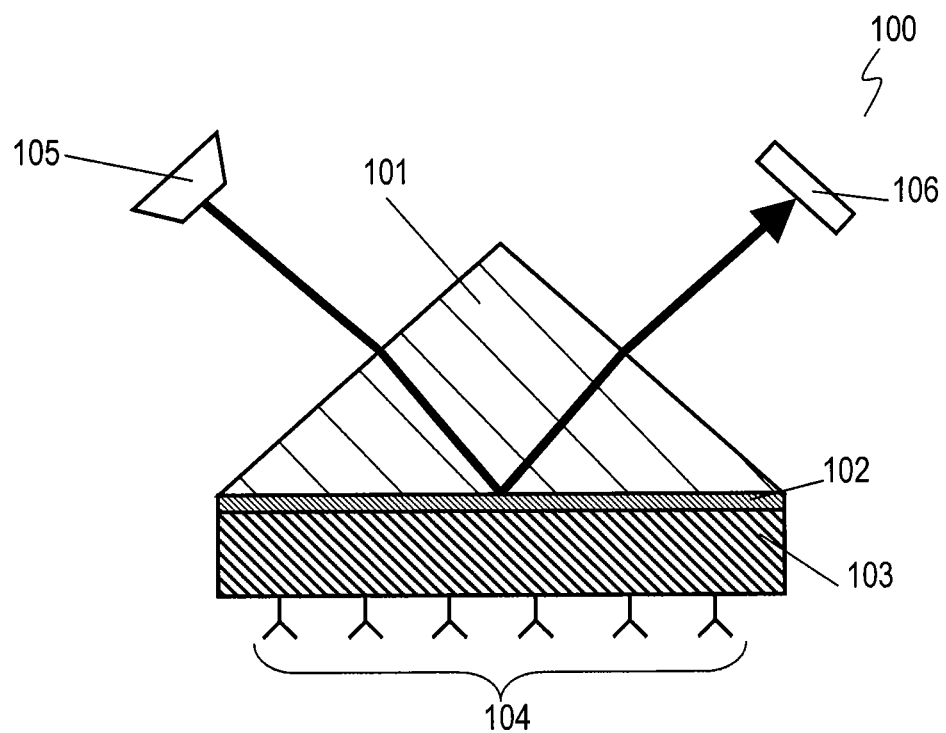
FIG. 28 is a cross-sectional view of a conventional plasmon sensor.

When using a conventional plasmon sensor shown in FIG. 28 by holding it with a hand, a person holding the plasmon sensor likely touches an area where ligands 104 are formed and surface plasmon resonance occurs, hence causing the resonance frequency to shift. In plasmon sensor 1 according to Embodiment 1, however, a person unlikely touches the area where surface plasmon resonance occurs, since the area is located on lower surface 2B of metal layer 2 and upper surface 3A of metal layer 3 facing hollow space 4, hence preventing any change in the resonance frequency.

It was confirmed by an electromagnetic field simulation that the resonance frequency did not change substantially even if the state of medium around upper surface 2A of metal layer 2 shown in FIGS. 3A and 3B was changed. It was also confirmed by the electromagnetic field simulation that the resonance frequency did not change substantially even when the state of medium around lower surface 3B of metal layer 3 changed.

Figure 10A:
FIG. 10A is a cross-sectional view of the plasmon sensor according to Embodiment 1 to illustrating a process for manufacturing the plasmon sensor.
Figure 10B:
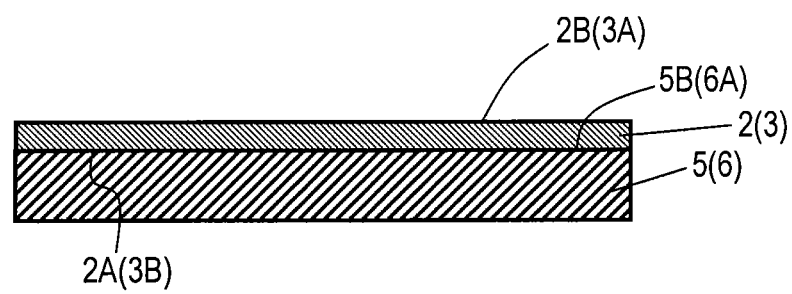
FIG. 10B is a cross-sectional view of the plasmon sensor according to Embodiment 1 to illustrating a process for manufacturing the plasmon sensor.
Figure 10C:
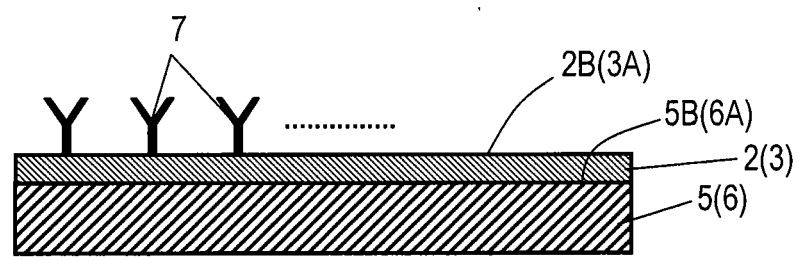
FIG. 10C is a cross-sectional view of the plasmon sensor according to Embodiment 1 to illustrating a process for manufacturing the plasmon sensor.

A method of manufacturing plasmon sensor 1 according to Embodiment 1 will be described below. FIGS. 10A to 10C are cross-sectional views of plasmon sensor 1 for illustrating the method of manufacturing the plasmon sensor 1.

Metal layer 2 is formed, as shown in FIG. 10B, by, e.g. a sputtering method or a deposition method on surface 5B of supporter 5 shown in FIG. 10A. Since the resonance frequency changes depending on the thickness and the material of metal layer 2, the optimum thickness and the metal material are selected according to a predetermined resonance frequency. The electromagnetic wave supplied from above upper surface 2A of metal layer 2 needs to pass through metal layer 2 and enter to hollow space 4 in order to generate surface plasmon resonance as shown in FIG. 1. The thickness and material of supporter 5 in addition to the thickness and material of metal layer 2 are elected to enable the above operation.

Next, ligands 7 are fixed to surface 2B of metal layer 2 by a physical method or a chemical method, as shown in FIG. 10C.

Metal layer 3 is formed on surface 6A of supporter 6 by the sputtering method, deposition method or the like process as shown in FIG. 10B. Ligands 7 are then fixed to upper surface 3A of metal layer 3 as shown in FIG. 10C.

Figure 11A:
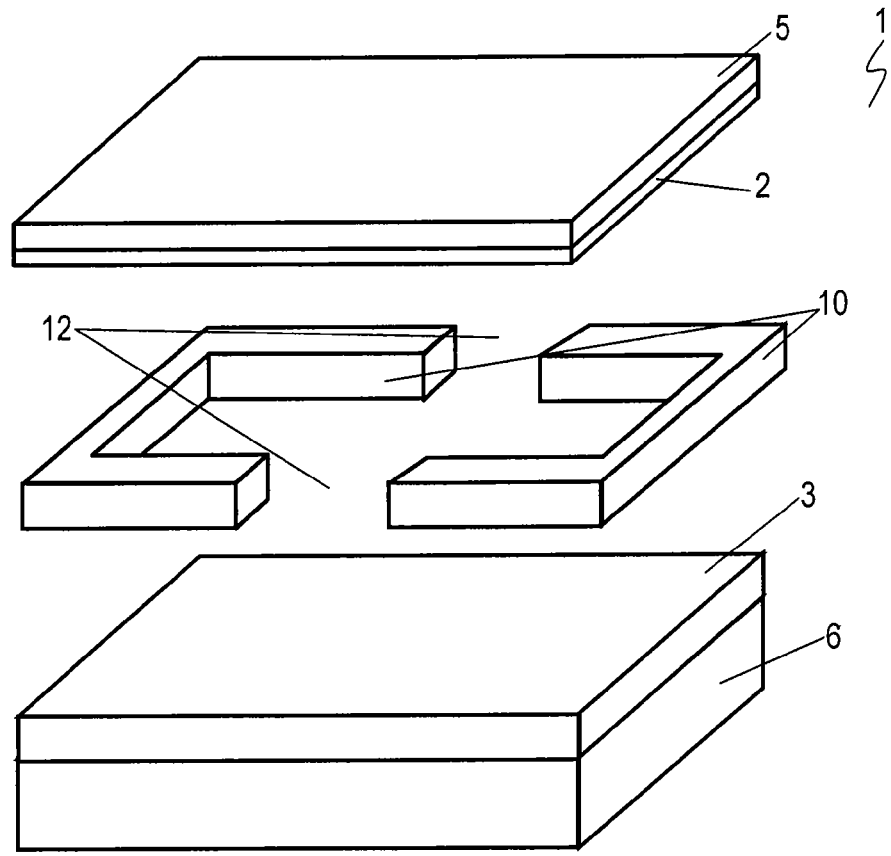
FIG. 11A is an exploded perspective view of the plasmon sensor according to Embodiment 1.
Figure 11B:
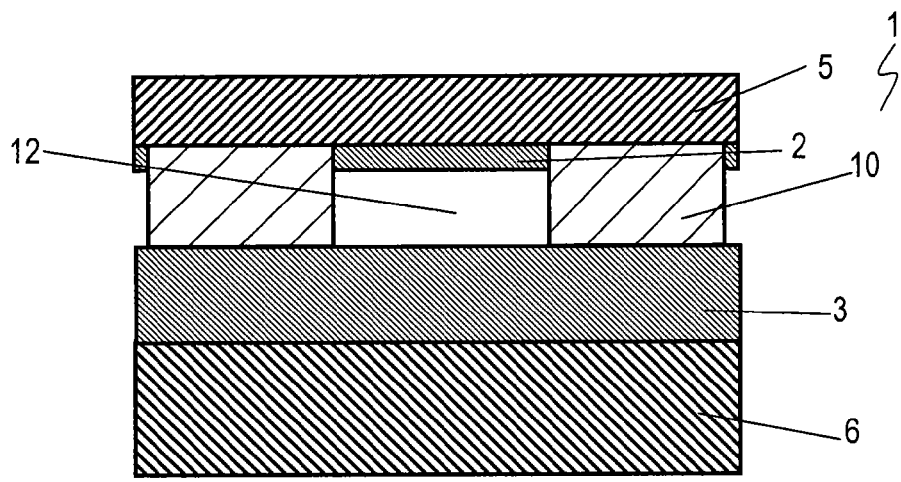
FIG. 11B is a cross-sectional view of the plasmon sensor according to Embodiment 1.

A method of manufacturing plasmon sensor 1 will be described below. FIGS. 11A and 11B are an exploded perspective view and a cross-sectional view of plasmon sensor 1, respectively, for illustrating the method of manufacturing the plasmon sensor 1. Metal layers 2 and 3 formed in the above processes are retained with a space of a given distance between them by walls 10 as spacers.

Walls 10 are made of, e.g. a metal or a dielectric material which is processed by etching, or formed by deposition after the surface is masked. Walls 10 may be made of the same material as metal layers 2 and 3 to improve adhesion of metal layer 2 to walls 10 and metal layer 3 to walls 10. Alternatively, an adhesive layer may be provided in each of interfaces between metal layer 2 and walls 10 and between metal layer 3 and walls 10 to improve the adhesion of metal layer 2 to walls 10 and metal layer 3 to walls 10.

Figure 12A:
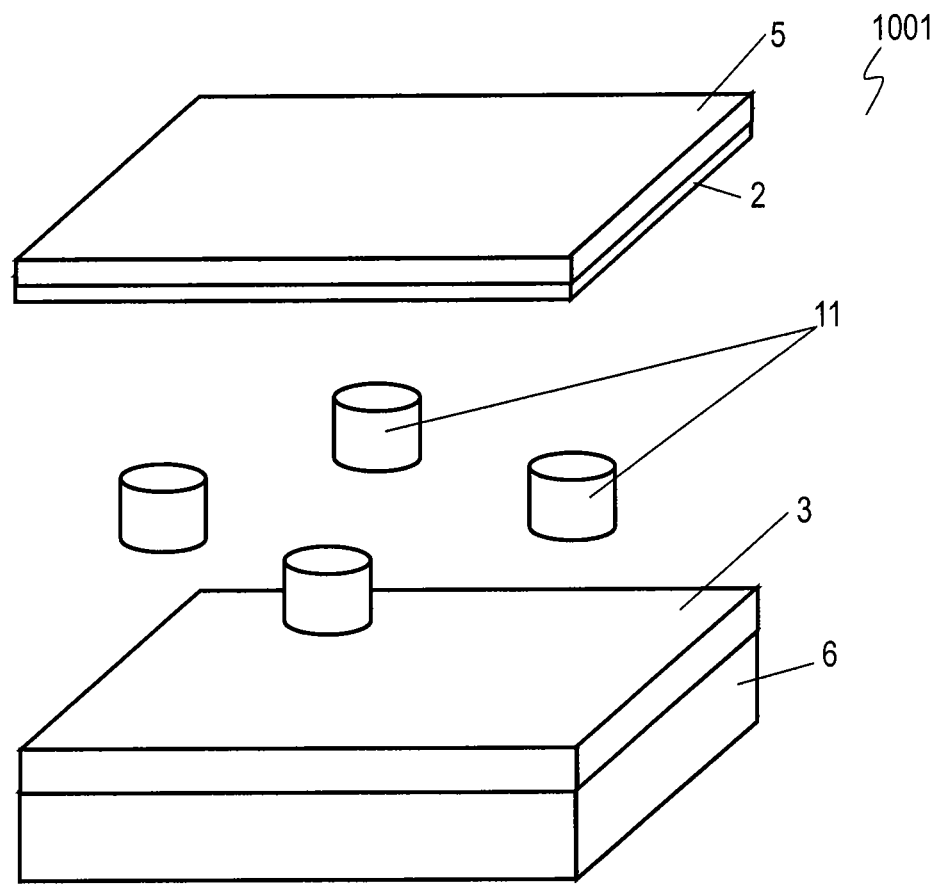
FIG. 12A is a perspective view of another plasmon sensor according to Embodiment 1.
Figure 12B:
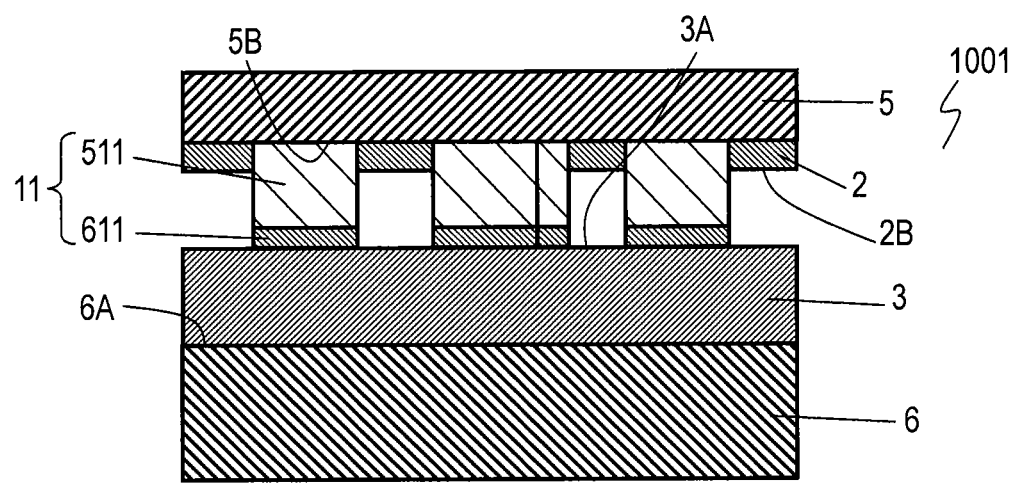
FIG. 12B is a cross-sectional view of the plasmon sensor shown in FIG. 12A.

FIGS. 12A and 12B are an exploded perspective view and a cross-sectional view of another plasmon sensor 1001 according to Embodiment 1, respectively, for illustrating the method of manufacturing sensor 1001. In FIGS. 12A and 12B, components identical to those of plasmon sensor 1 shown in FIGS. 11A and 11B are denoted by the same reference numerals. Plasmon sensor 1001 includes plural posts 11 serving as spacers instead of walls 10. Posts 11 retain metal layers 2 and 3 with a space of a given distance between layers 2 and 3.

Posts 11 are made of a metal or a dielectric material which is processed by etching, or formed by deposition after the surface is masked. Posts 11 may be made of the same material as metal layers 2 and 3 to improve adhesion of metal layer 2 to posts 11 and metal layer 3 to posts 11. Alternatively, an adhesive layer may be provided in each of interfaces between metal layer 2 and posts 11 and between metal layer 3 and posts 11 to improve the adhesion of metal layer 2 to posts 11 and metal layer 3 to posts 11.

The spacers (walls 10 or posts 11) may include at least two layers. One of these layers at one side is made of the same material as at least one of metal layers 2 and 3, and a thickness of this layer is smaller than a thickness of the other layer. When the spacers includes three or more layers, all layers other than one-side layer have a total thickness corresponding to the thickness of the other layer in the above two-layer structure. Such a design has an advantage, which will be described below, A method of manufacturing the structure shown in FIG. 12B as an example will be described below. A mask having holes in areas corresponding to posts 11 is formed on lower surface 5B of supporter 5, and then, titanium is deposited to form titanium layers 511 of posts 11. Layers 511 correspond to the other layer in the above two-layer structure. The mask is removed, and then gold is deposited on an area of supporter 5 where layers 511 are not formed and at least the lower surfaces of layers 511. This process provides layers 611 of posts 11 made of gold on the lower surfaces of layers 511. Layers 611 are made of the same material as metal layer 2, and they correspond to the one-side layer in the above two-layer structure. The gold layer formed in the area where layers 511 of posts 11 are not formed makes up metal layer 2. Gold layers 611 of posts 11 are designed to have the thickness smaller than the thickness of titanium layers 511 of posts 11. Gold layers 611 of posts 11 have a conductivity higher than that of layers 511 of posts 11. Gold layers 511 of posts 11 are harder than titanium layers 611 of posts 11.

Gold is deposited on upper surface 6A of supporter 6 to form metal layer 3 made of gold. Metal layer 3 is hence made of the same metal as those used for metal layer 2 and layers 611 of posts 11. Subsequently, the lower surfaces of layers 611 of posts 11 are bonded to upper surface 3A of metal layer 3 to fix posts 11 to metal layer 3. Layers 611 of posts 11 and metal layer 3 are bonded securely to each other since they are made of the same metal, thereby improving the physical strength of plasmon sensor 1001. In addition, the titanium of layers 511 mainly constituting posts 11 provides robustness of posts 11 since titanium is harder than gold of layers 611, and increases the physical strength of plasmon sensor 1001. This structure allows a less expensive metal to be used to form layers 511 than the metal of high conductivity and relatively high cost used for layers 611 since layers 511 of posts 11 are not required to have such a high conductivity compared with metal layer 2, metal layer 3, or layers 611 of posts 11. Layers 511 mainly constitute posts 11, hence providing plasmon sensor 1001 with low cost. Furthermore, this structure improves the productivity since layers 611 of posts 11 can be formed simultaneously with metal layer 2 in the same process of deposition. This structure also improves the adhesion between posts 11 and metal layer 3 since layers 611 of posts 11 can be made of the same metal as metal layer 3.

Metal layer 3 may be formed after forming the titanium layer by depositing titanium on upper surface 6A of supporter 6, and depositing gold on the surface of the titanium layer. This method allows plasmon sensor 1001 to be manufactured inexpensively by designing the gold layer such that the gold layer is thinner than the titanium layer formed on upper surface 6A of supporter 6. In the above embodiment, titanium is used for layers 511 and gold is used for layers 611 and metal layers 2 and 3. However, a similar advantage can be achieved so long as the same metal material is used for layers 611 and metal layers 2 and 3.

In addition, a similar advantageous effect is also obtainable by applying the above-discussed structure of posts 11 shown in FIG. 12B to the structure of walls 10 shown in FIG. 11B.

After metal layer 2 is formed by depositing gold, ligands 7 can be fixed onto lower surface 2B of metal layer 2. Ligands 7 may also be fixed onto upper surface 3A of metal layer 3 after metal layer 3 is formed by depositing gold. The lower surfaces of layers 611 of posts 11 and upper surface 3A of metal layer 3 can be bonded together after these processes to complete plasmon sensor 1001. The bonding surfaces are to be cleaned to remove dirt (such as ligands) before bonding the gold layers formed on the end surfaces of posts 11 and metal layer 2 to ensure proper connections between these gold layers. In an alternative method, lower surfaces of layers 611 of posts 11 and metal layer 3 are bonded before ligands 7 are fixed to the surface of any of metal layers 2 and 3. Ligands 7 are then fixed to the surface of any of metal layers 2 and 3 by injecting a liquid containing ligands 7 into hollow space 4 by capillary phenomenon.

Plasmon sensor 1001 may have a configuration in which the spacers, either walls 10 or posts 11, are fixed with their end portions inserted in at least one of metal layers 2 and 3. That is, at least one of upper surface (end portion) and bottom surface (end portion) of each of posts 11 is inserted in and fixed to at least one of metal layers 2 and 3, as shown in FIG. 12A. In FIG. 12A, the upper surfaces of posts 11 are inserted in metal layer 2. The end portions of posts 11 may be tapered sharply or lower surface 2B of metal layer 2 may be provided with guide holes to help the end portions of posts 11 inserted easily in metal layer 2. This process can eliminate the removing of the ligands previously from the areas of metal layer 2 where the end portions of posts 11 contact the ligands by inserting posts 11 in metal layer 2 and fixing them together. The gold layers formed at the end portions of posts 11 and the gold layer of metal layer 2 are not easily bonded if, for instance, dirt (such as ligands) on the bonding surfaces of these gold layers are not cleaned in advance when bonding these gold layers. This method can simplify the manufacturing process and provides inexpensive plasmon sensor 1001.

The height of walls 10 or posts 11 is determined in consideration of the desired resonance frequency for generating the surface plasmon resonance.

In addition, the structure may be so designed that a distance from one wall 10 to other walls 10 or from one post 11 to other posts 11 is to be larger than the resonant wavelength. This arrangement prevents the sensitivity of plasmon sensor 1 from decreasing due to excitation of undesired surface plasmon resonance attributable to the structure having walls 10 or posts 11. Ligands 7 may not be fixed to all the surfaces where walls 10 are bonded to metal layer 2 and metal layer 3. This structure can improve the adhesion between walls 10 and metal layer 2 as well as between walls 10 and metal layer 3.

Alternatively, ligands 7 may be fixed to the entire surface at one side of metal layer 2 and also the entire surface at one side of metal layer 3. This can avoid the need to form two distinct forms of areas, one with ligands 7 fixed to it and the other without ligands 7, and improve the manufacturing efficiency.

In FIGS. 10A to 10C, although ligands 7 are fixed to both of metal layers 2 and 3, ligands 7 may be arranged on at least one of metal layers 2 and 3. This also improves the manufacturing efficiency when ligands 7 are arranged only on one of metal layers 2 and 3.

Ligands 7 can be fixed onto metal layers 2 and 3 by another method in which a self-assembled monolayer (SAM) is first formed on the surfaces of metal layers 2 and 3, and then, ligands 7 are fixed on the surfaces of the SAM. The SAM may preferably contain an organic substance having sulfide radical or thiol radical. This organic substance is dissolved in a solvent, such as ethanol, to make a solution. Metal layers 2 and 3 cleaned with UV ozone are immersed in this solution for several hours. After metal layers 2 and 3 are taken out of the solution, they are cleaned with the solvent used for making the solution, and then cleansed with pure water. The above processes can form the SAM on the surfaces of metal layers 2 and 3.

After hollow space 4 is formed by the above processes, a ligand solution is prepared by dissolving ligands in a solvent, such as ethanol, similarly to the SAM. The ligand solution is injected into hollow space 4 by capillary phenomenon. This process causes the ligands to covalent bond with the SAM, which is also bonded covalently to the surfaces of metal layers 2 and 3, and to fix ligands 7 to these surfaces.

Next, the liquid solution is evaporated with heat applied from the outside to remove the liquid solution remaining in hollow space 4. Or, the remaining solution may be expelled by a centrifugal force with using a spin-coater. The ligands left out of the covalent bonding with the SAM can be rinsed off when the spin coater is used since metal layers 2 and 3 can be cleaned with the same solvent as used for the ligand solution and cleansed with pure water.

Note that FIGS. 11A, 11B, 12A and 12B do not illustrate ligands 7 for simple illustration.

Walls 10 and posts 11 may be made of the same material as metal layers 2 and 3, thereby increasing adhesion of walls 10 or posts 11 and metal layers 2 and 3.

In addition, a material, such as titanium, having a property of improving adhesion may be provided between supporter 5 and metal layer 2 as well as between supporter 6 and metal layer 3 in order to improve the adhesion between these components. This material prevents metal layers 2 and 3 from being peeled off from supporters 5 and 6 when walls 10 and posts 11 are attached to metal layers 2 and 3 with a pressure.

An exemplary method of the above processes will be described below.

(Step 1)

A first film is formed on lower surface 5B of supporter 5 made of, e.g. glass by electron-beam evaporation (i.e., EB deposition) in order to form walls 10 or posts 11 on lower surface 5B of supporter 5. Before performing the EB deposition, a mask is placed on lower surface 5B of supporter 5 to cover areas other than where walls 10 or posts 11 are formed to prevent the first film from covering the areas where the plasmon resonance is generated.

The first film includes two layers, one made of gold (Au) and the other made of titanium (Ti). The first film can be configured by forming a titanium layer on lower surface 5B of supporter 5, and then, forming a gold layer on the surface of the titanium layer. The titanium layer is used as a bonding layer for increasing the adhesion between the glass and the gold layer that constitute supporter 5 and walls 10 or posts 11, respectively.

Next, a gold layer is formed on the surfaces of supporter 5 and the first film by using the EB deposition after the mask is removed. This process forms metal layer 2 on the areas where the mask is removed. Though this process forms a gold layer on the surfaces of walls 10 or posts 11, this gold layer makes gold-to-gold bonding with the other gold layers already covering the surfaces of the first film constituting walls 10 or posts 11, and it thus has a very high level of adhesion.

In the case that metal layer 2 is not formed immediately after the first film is formed, the surface the first film is prone to being covered with carbon in the air, and tends to weaken the adhesion of metal layer 2 to the gold layer on the surface of the first film. The carbon is preferably removed from the surfaces of the first film and supporter 5 by, e.g. a plasma treatment before depositing metal layer 2.

On the other hand, metal layer 3 is formed on upper surface 6A of supporter 6 made of glass, for instance, by EB deposition. Metal layer 3 includes two layers of gold and titanium similar to the first film, and can be configured by forming a titanium layer first on upper surface 6A of supporter 6, and then a gold layer on the surface of the titanium layer. The titanium layer is used as a bonding layer for increasing the adhesion between supporter 6 and the gold that constitutes metal layer 3. The titanium layer is also used as the bonding layer between the glass and the gold that constitute supporter 5 and walls 10 or posts 11 respectively to increase their adhesion.

Supporters 5 and 6 provided with walls 10 or posts 11 are completed with the above processes.

When walls 10 or posts 11 are formed on supporter 6, metal layer 2 on lower surface 5B of supporter 5 is formed preferably only with a thin film of gold. If a titanium layer is provided to serve as a bonding layer, it inflicts a loss on the surface plasmon resonance since titanium has a lower conductivity than gold. It is thus possible to improve the sensitivity of plasmon sensor 1 by not providing the titanium layer. The layer of gold on metal layer 2 is prone to be peeled off when walls 10 or posts 11 are bonded to metal layer 2. Walls 10 or posts 11 are preferably formed on metal layer 2 by deposition. The titanium layer can be formed simply on the surfaces of metal layer 2 where walls 10 or posts 11 are provided since the surface plasmon resonance is not likely to occur in these surfaces.

(Step 2)

The surfaces of walls 10 or posts 11 on supporter 5 are bonded to the surface of metal layer 3 on supporter 6 by gold-to-gold bonding. Since the both surfaces of walls 10 and posts 11 and the surface of metal layer 3 are made of gold, they can be bonded securely.

Carbon covering the surfaces of walls 10 or posts 11 and metal layer 3 is preferably removed by performing a plasma treatment on these surfaces, for instance, before making the gold-to-gold bonding.

The above process securely retains supporters 5 and 6 together by the metal bonding between the surfaces of walls 10 or posts 11 and the surface of metal layer 3, providing the structure shown in FIG. 11B or 12B.

When plasmon sensors 1 and 1001 manufactured by the method illustrated from FIGS. 10A to 12B are used, it is necessary to change the state of the medium inside hollow space 4 between metal layers 2 and 3.

In order to change the state of the medium inside hollow space 4, a test sample (such as gas or liquid) containing an analyte is injected into hollow space 4. Plasmon sensor 1 is therefore provided with two sample injection ports 12 for this purpose as shown in FIG. 11A.

The medium in hollow space 4 may be sucked through one of sample injection ports 12 in order to introduce the test sample into hollow space 4 from the other sample injection port 12.

Alternatively, the test sample may be injected from one of sample injection ports 12 by expanding the test sample with heat and using an expansion force of it.

The test sample can also be injected from one of sample injection ports 12 by using a small pump made of a piezoelectric ceramic or the like element.

Moreover, if the test sample is a liquid, the test sample can be injected from one of sample injection ports 12 by vibrating plasmon sensor 1 while being tilted to such a position that both surfaces 2B and 3A of metal layers 2 and 3 are not perpendicular to the direction of the gravity.

Furthermore, the test sample can be injected from one of sample injection ports 12 by ionizing the test sample, or the analyte in particular, and exerting either a magnetic field or an electric field on it from the outside.

Figure 13A:
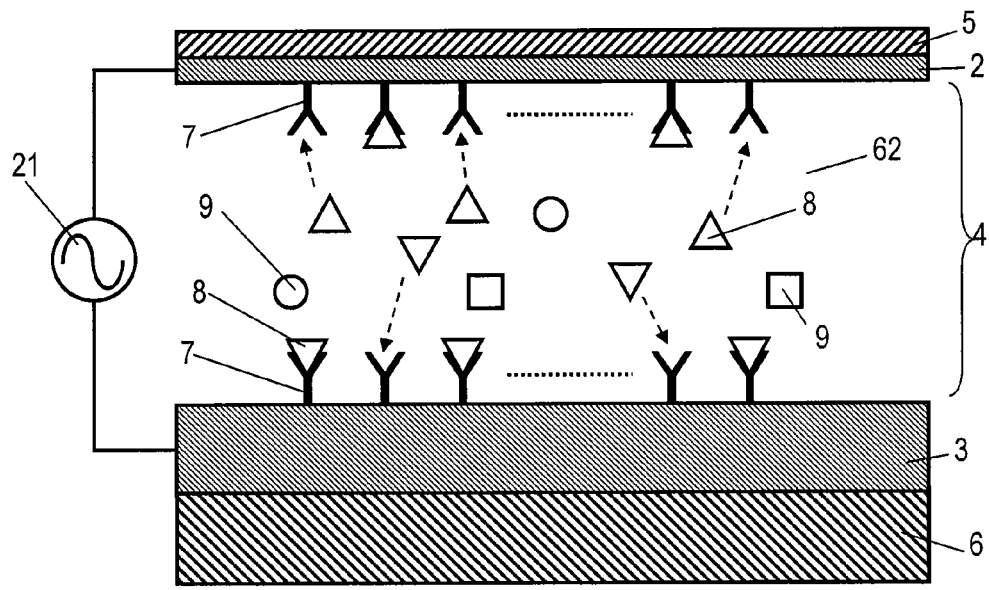
FIG. 13A is a cross-sectional view of the plasmon sensor according to Embodiment 1.

FIG. 13A is a cross-sectional view of plasmon sensor 1 for illustrating a method of using plasmon sensor 1 by exerting an electric field from the outside.

Metal layer 2 having ligands 7 disposed on lower surface 2B is fixed to supporter 5. Metal layer 3 facing metal layer 2 has ligands 7 on upper surface 3A, and is fixed to supporter 6. An alternating-current (AC) voltage from AC power source 21 is applied between metal layers 2 and 3.

Hollow space 4 between metal layers 2 and 3 is filled with test sample 62 containing target analyte 8 and non-specific binding analyte 9. Analyte 8 is at least ionized to either a negative side or a positive side.

When a positive voltage is applied to metal layer 2 and a negative voltage is applied to metal layer 3 with analyte 8 ionized to the negative side, for instance, analyte 8 is attracted toward metal layer 2, thereby facilitating specific binding of analyte 8 with ligands 7 fixed to metal layer 2.

After a lapse of time period that changes the polarities of the AC voltage supplied from AC power source 21, or half the cycle of the AC voltage, the negative voltage is applied to metal layer 2 and the positive voltage is applied to metal layer 3. Analyte 8 is then attracted toward metal layer 3, thereby facilitating specific binding of analyte 8 with ligands 7 fixed to metal layer 3. This allows ligands 7 to be fixed effectively to metal layers 2 and 3 and analyte 8 in test sample 62.

The period of the AC power voltage is determined based on a movable speed of analyte 8 between metal layers 2 and 3.

In the case that ligands 7 are fixed to only one of metal layers 2 and 3, the voltage applied between metal layers 2 and 3 can be a direct-current (DC) voltage, hence simplifying a structure of the power source.

Figure 13B:
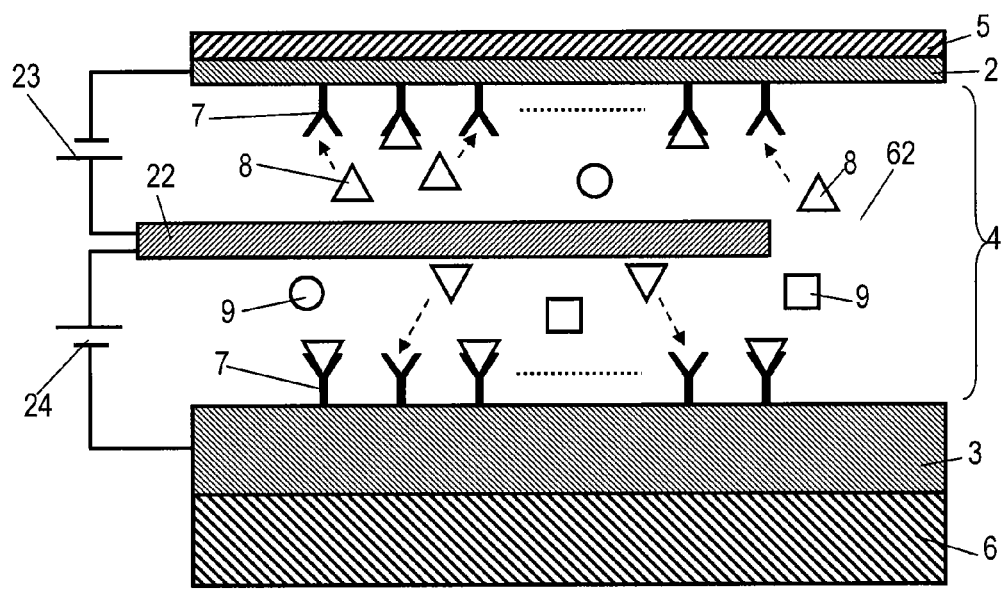
FIG. 13B is a cross-sectional view of the plasmon sensor according to Embodiment 1.

FIG. 13B is a cross-sectional view of plasmon sensor 1 for illustrating another method of using plasmon sensor 1 by exerting an electric field from the outside. In FIG. 13B, electrode 22 is inserted and fixed in hollow space 4. DC power source 23 is connected between electrode 22 and metal layer 2. DC power source 24 is connected between electrode 22 and metal layer 3.

Since ligands 7 are ionized to the positive side, analyte 8 ionized to the negative side is attracted toward both metal layers 2 and 3 charged with a voltage of a potential negative with respect to electrode 22. This allows the specific binding effectively between ligands 7 and analyte 8.

FIGS. 13A and 13B do not illustrate walls 10 and posts 11 for simple illustration. It is practical that posts 11 or walls 10 retaining metal layers 2 and 3 may also be used to support electrode 22.

In another structure, ligands 7 are disposed to at least one of adjacent region 502B, which is an area around lower surface 2B of metal layer 2 and adjacent region 503A, which is another area around upper surface 3A of metal layer 3. This structure allows ligands 7 to contact analyte 8 while metal layers 2 and 3 are separated without being fixed to each other by spacers, such as walls 10 and posts 11. Then, metal layers 2 and 3 are fixed to their predetermined positions by the spacers. Plasmon sensor 1 manufactured by the above steps can easily allow ligands 7 to contact analyte 8.

Figure 14A:
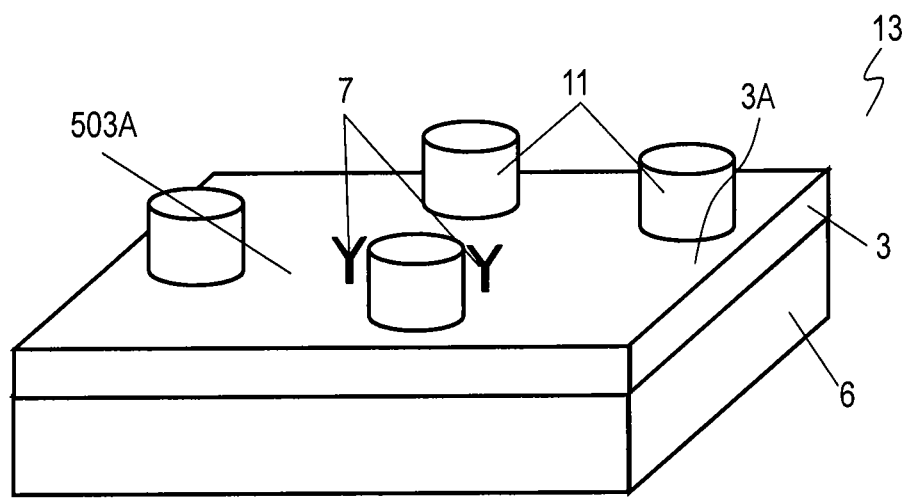
FIG. 14A is a partial perspective view of the plasmon sensor according to Embodiment 1.
Figure 14B:
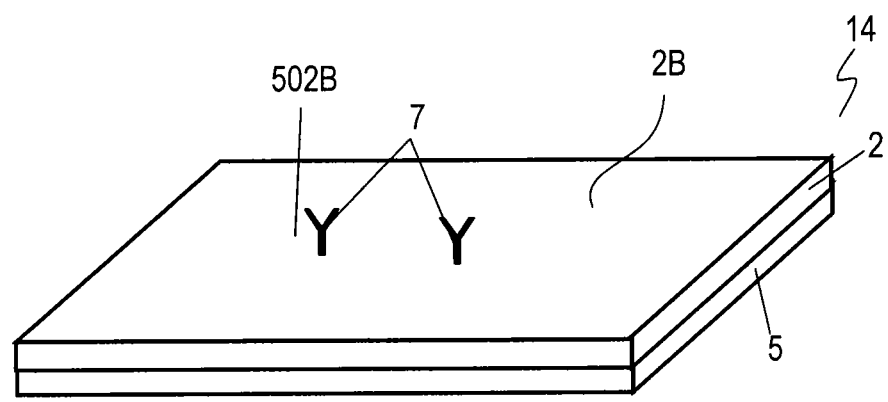
FIG. 14B is a partial perspective view of the plasmon sensor according to Embodiment 1.

FIG. 14A is a perspective view of component member 13 including supporter 6, metal layer 3, and posts 11 which are unitarily formed. FIG. 14B is a perspective view of component member 14 including supporter 5 and metal layer 2 which are unitarily formed. In plasmon sensor 1, first component member 13 is first separated from second component member 14.

First, ligands 7 disposed on upper surface 3A of metal layer 3 shown in FIG. 14A contact test sample containing analyte 8. Ligands 7 disposed on surface 2B of metal layer 2 shown in FIG. 14B contact test sample containing analyte 8.

After that, component member 13 shown in FIG. 14A and component member 14 shown in FIG. 14B are fixed with posts 11, completing the assembling of plasmon sensor 1001 shown in FIG. 12B.

Subsequently, light is irradiated to metal layer 2 from a light source located above supporter 5 shown in FIG. 12B, and a state of specific binding between the ligands and the analyte is detected by receiving a reflected light or radiated light with a detector unit located above supporter 5 and measuring the change in the amount of received light.

To be more specific, a resonance frequency shifts when a change occurs in the medium (i.e., changes in value of the relative dielectric constant and distribution of the relative dielectric constant) inside hollow space 4 due to the specific binding between the ligands and the analyte, and it results in a change in the amount of the light reflected or radiated from plasmon sensor 1. The state of specific binding between ligands 7 and analyte 8 can be detected by measuring the amount of the light reflected or radiated from plasmon sensor 1.

Plasmon sensor 1 manufactured by the above method can easily cause ligands 7 to contact analyte 8.

In FIGS. 14A and 14B, component member 13 includes posts 11, but this is not restrictive as such that component member 14 may have posts 11, or both first component member 13 and second component member 14 may includes posts 11.

Sample injection port 12 is a portion where hollow space 4 faces an area outside of the space confined between metal layers 2 and 3, from which the test sample can be injected into hollow space 4.

The test sample may be a fluid, such as gas or liquid, containing analyte or not containing analyte. The test sample can be a fluid, such as gas or liquid, not containing analyte 8 if plasmon sensor 1 does not include ligands 7.

Adjacent region 502B is an area adjacent to surface 2B of metal layer 2 at the side facing hollow space 4. The resonance frequency shifts due to a change in the medium in this area. More specifically, adjacent region 502B is the area on surface 2B of metal layer 2. When surface 2B of metal layer 2 is covered with a thin film of dielectric substance, adjacent region 502B is a surface of the thin film.

In addition, adjacent region 503A is an area adjacent to surface 3A of metal layer 3 at the side facing hollow space 4. The resonance frequency shifts due to a change in the medium in this area. More specifically, adjacent region 503A is the surface 3A of metal layer 3. When surface 3A of metal layer 3 is covered with a thin film of dielectric substance, adjacent region 503A is a surface of the thin film.

The condition that metal layers 2 and 3 are separated from each other is signifies that metal layers 2 and 3 are not fixed to their respective positions by the spacers, such as posts 11 and walls 10, but they are movable relatively with respect to each other.

Figure 15:
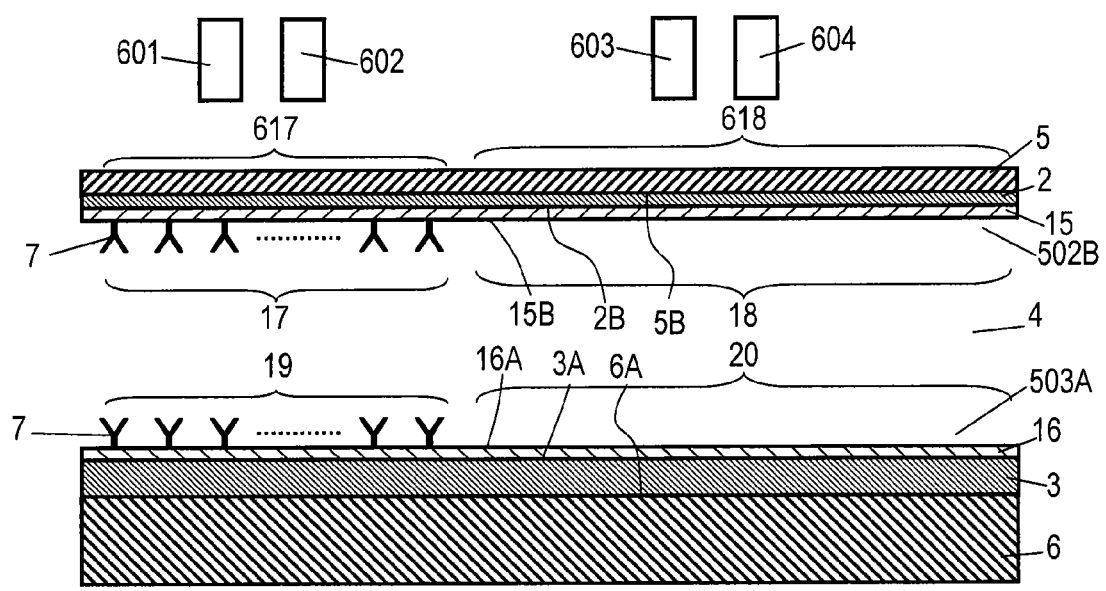
FIG. 15 is a cross-sectional view of the plasmon sensor according to Embodiment 1.

FIG. 15 is a cross-sectional view of plasmon sensor 1 in a configuration that metal layers 2 and 3 are separable. Here, adjacent region 502B has area 17 provided with ligands 7 and area 18 not provided with ligands 7. Adjacent region 503A has area 19 facing area 17 and provided with ligands 7, and area 20 facing area 18 and not provided with ligands 7.

When metal layers 2 and 3 are fixed to their respective positions by the spacers, such as posts 11 and walls 10, from the separated condition, there may be a variation of a spatial distance between metal layers 2 and 3. This provides a variation of a resonant wavelength of plasmon sensor 1. In this case, the resonant wavelength is found out at first when using the sensor.

Due to the above structure, even if the spatial distance varies between metal layers 2 and 3, the presence and absence of specific binding between the ligands and analyte can be detected by comparing amounts of reflected light or radiated light between when the light is irradiated to an area of supporter 5 facing area 17 or an area metal layer 2 facing area 17 and when the light is irradiated to an area of supporter 5 facing area 18 or an area of metal layer 2 facing area 18. This provides plasmon sensor 1 with high accuracy.

In FIG. 15, metal layer 2 is disposed on lower surface 5B of supporter 5. Protective layer 15 is formed on lower surface 2B of metal layer 2 to prevent metal layer 2 from corrosion. Ligands 7 are fixed onto area 17 of lower surface 15B pf protective layer 15. Area 19 substantially faces area 17. On the other hand, ligand 7 is not provided on area 18 of lower surface 15B.

Metal layer 3 is disposed on upper surface 6A of supporter 6. Protective layer 16 is formed on upper surface 3A of metal layer 3 to prevent metal layer 3 from corrosion. Ligands 7 are fixed onto area 19 of upper surface 16A of protective layer 16. Area 19 substantially faces area 17. On the other hand, ligand 7 is not provided on area 20 of upper surface 16A. Area 20 substantially faces second area 18.

Light, an electromagnetic wave is irradiated from light source 601 ζ area 617 which is located above upper surface 2A of metal layer 2 and which faces area 17. At this moment, detector unit 602 receives the light reflected or radiated.

Similarly, light, electromagnetic wave is irradiated from light source 603 to area 618 which are located above upper surface 2A of metal layer 2 and which faces area 18. At this moment, detector unit 604 receives the light reflected or radiated.

The light may be irradiated alternately to areas 617 and 618. This can prevent detector unit 604 from receiving the light irradiated to and reflected or radiated off area 617, and prevents detector unit 602 from receiving the light irradiated to and reflected or radiated off area 618.

Light source 601 irradiate the light only to area 617, and the light is stopped irradiating from light source 601 after the specific binding of ligands 7 and analyte 8 is positively confirmed. Then, light source 603 irradiates light only to area 618. This method prevents detector unit 604 from receiving the light irradiated to and reflected or radiated off area 617, and prevents detector unit 602 from receiving the light irradiated to and reflected or radiated off area 618, as stated above, while measuring the progress of specific binding without interruption. The light reflected or radiated from area 618 can be used to obtain a reference value when the light is irradiated only to area 618 after the specific binding is performed.

Areas 17 and 18 have sizes sufficiently larger than the resonant wavelength. For example, each of the sides of areas 17 and 18 has a length more than twice the resonant wavelength. This structure reliably isolates the surface plasmon resonance occurring in areas 17 and 19 from the surface plasmon resonance occurring in areas 18 and 20.

In the configuration that metal layers 2 and 3 are separable, the specific binding between ligands 7 and analyte 8 advances during the process of assembling metal layers 2 and 3, in which metal layer 2 is fixed to metal layer 3 by combining metal layers 2 and 3 together. The specific binding between ligands 7 and analyte 8 is preferably suppressed by supplying a magnetic field or an electric field from the outside in order to retard advancement of the specific binding between ligands 7 and analyte 8 as much as possible during the assembling process.

In FIG. 15, for instance, the electric field or the magnetic field is applied from the outside until completion of the process of fixing metal layers 2 and 3 to their predetermined positions so that one side at areas 18 and 20 have a positive polarity and the other side at areas 17 and 19 have a negative polarity when analyte 8 is ionized to the negative side. In this instance, the electric field or the magnetic field is applied externally instead of applying a voltage directly to metal layers 2 and 3 as shown in FIGS. 13A and 13B. Analyte 8 is attracted to one side at areas 18 and 20 in this manner so as to impede the specific binding of ligands 7 and analyte 8 during the process of assembling metal layers 2 and 3.

In the structure shown in FIGS. 14A and 14B, each of adjacent regions 502B and 503A may have an area which does not include ligand 7. Before metal layers 2 and 3 are assembled, the analyte can be attracted to the area which does not include ligand 7 by applying electric field or magnetic field from the outside.

Figure 16:
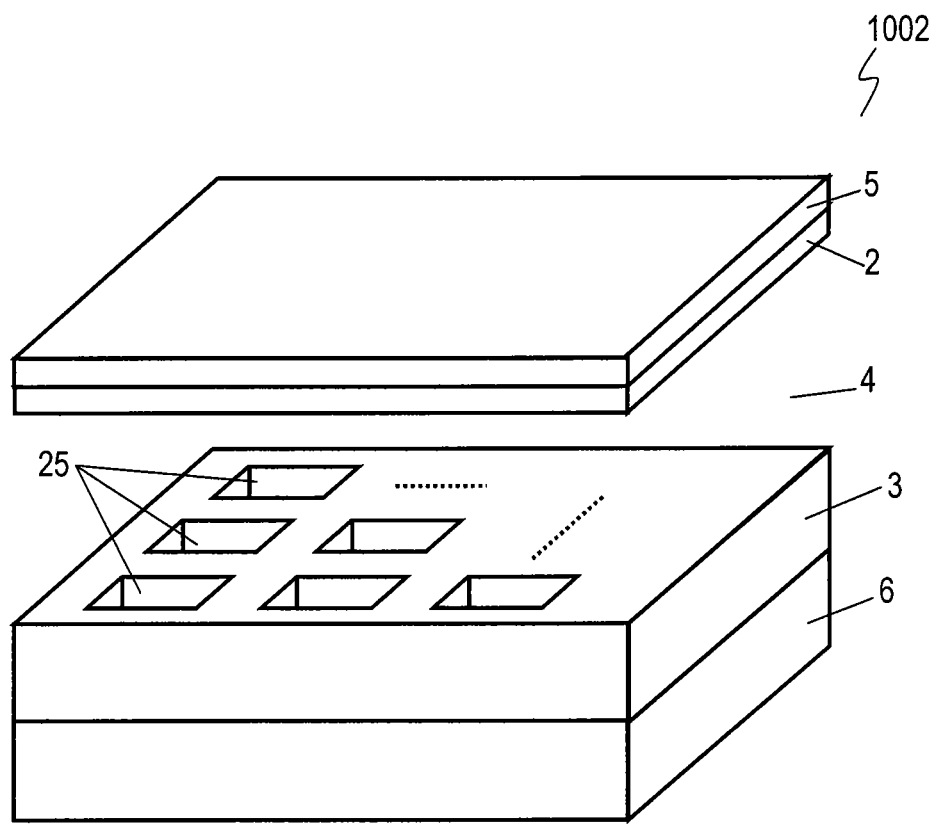
FIG. 16 is a perspective view of still another plasmon sensor according to Embodiment 1.

FIG. 16 is a perspective view of still another plasmon sensor 1002 according to Embodiment 1. In FIG. 16, components identical to those of plasmon sensor 1 shown in FIG. 1 are denoted by the same reference numerals. In plasmon sensor 1002 shown in FIG. 16, through-holes 25 are provided in metal layer 3 and supporter 6.

Through-holes 25 are used to inject a test sample containing analyte 8, for instance, into hollow space 4, thus facilitating the injection of the test sample in hollow space 4.

Figure 17:
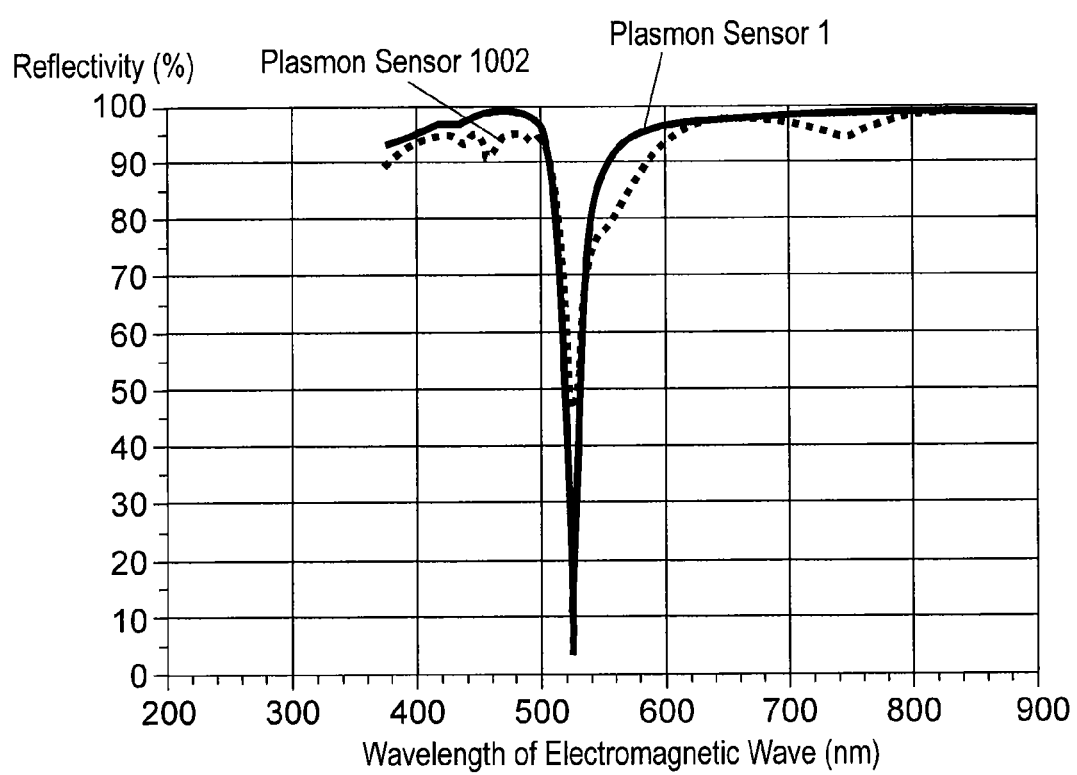
FIG. 17 shows an analysis result of a simulation of the plasmon sensor according to Embodiment 1.

FIG. 17 shows an analysis result of an electromagnetic field simulation performed on an analysis model of plasmon sensor 1102. This analysis model has the same configuration as the analysis model shown in FIG. 4A except for through-holes 25 which have a size of 150 nm by 150 nm and which are arranged in metal layer 3 regularly at intervals of 300 nm.

As shown in FIG. 17, a resonant wavelength of the sensor having through-holes 25 is substantially equal to the resonant wavelength of the other sensor not having through-holes 25, indicating that through-holes 25 provided in metal layer 3 does not significantly influence the surface plasmon resonance.

Exemplary Embodiment 2

Figure 18:
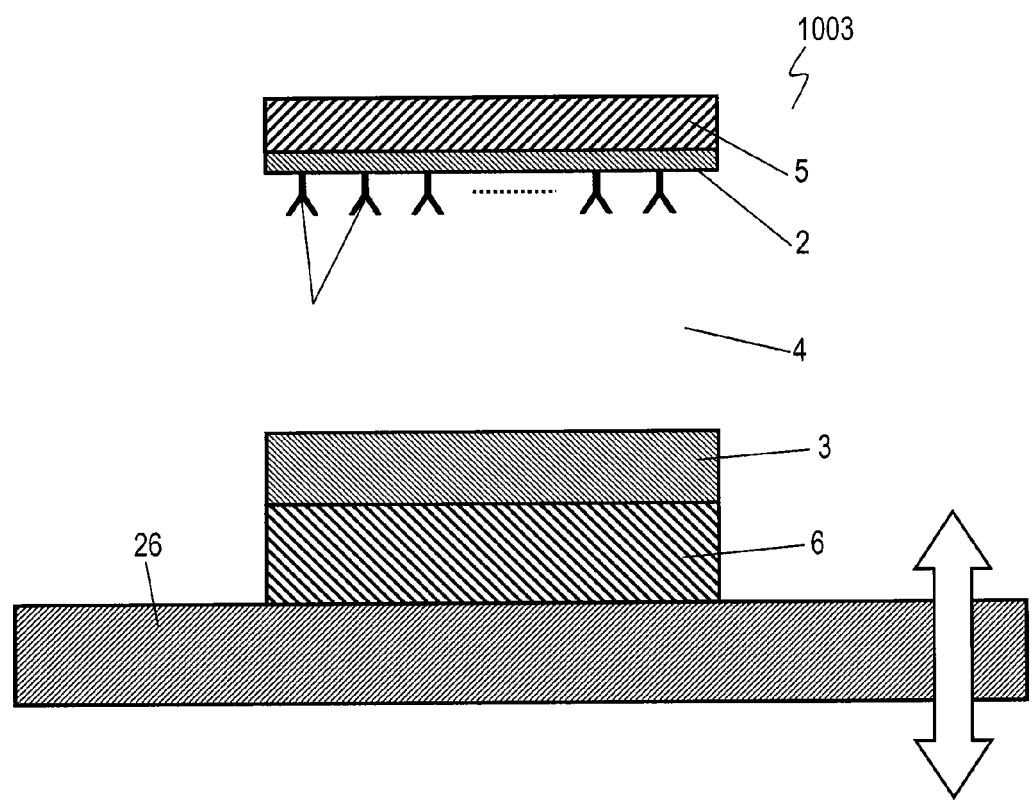
FIG. 18 is a cross-sectional view of a plasmon sensor according to Exemplary Embodiment 2 of the invention.

FIG. 18 is a cross-sectional view of plasmon sensor 1003 according to Exemplary Embodiment 2. In FIG. 18, components identical to those of plasmon sensor 1 shown in FIG. 1 are denoted by the same reference numerals. Plasmon sensor 1003 shown in FIG. 18 further includes movable stage 26 that retains supporter 6 of plasmon sensor 1 shown in FIG. 1. Movable stage 26 is an adjusting mechanism having a position movable at least in a vertical direction, and capable of changing the spatial distance between metal layers 2 and 3.

An operation of plasmon sensor 1003 will be described below. The space between metal layers 2 and 3 is widened to an extent sufficient for allowing the test sample to enter inside of hollow space 4 by moving movable stage 26. Then, plasmon sensor 1003 entirely contacts a test sample containing analyte 8. This operation allows the test sample to enter into hollow space 4. At this moment, an electric field, a magnetic field, heat, or vibration can be applied from the outside to facilitate the entering of the test sample in hollow space 4, as discussed above.

Then, movable stage 26 is moved and hold metal layer 3 at a position where surface plasmon resonance occurs.

After that, the state of specific binding between ligands 7 and analyte 8 is measured by irradiating electromagnetic wave from above metal layer 2 to detect the reflected wave or radiated wave similarly to plasmon sensor 1 according to Embodiment 1.

Plasmon sensor 1003 shown in FIG. 18 thus has a resonant wavelength adjustable by changing the position of movable stage 26.

When the state of the medium in hollow space 4 changes due to the specific binding between ligands 7 and analyte 8, the position of movable stage 26 can be adjusted such that the resonant wavelength maintains constant. This operation allows the state of the specific binding to be monitored according to the change in the position of movable stage 26, or a speed of the change of the position.

If light of only a single wavelength is monitored, the state of specific binding occurring at a wavelength other than that of the light cannot be monitored. Plasmon sensor 1003 according to Embodiment 2 is thus designed to produce the plasmon resonance by light of plural wavelengths.

In plasmon sensor 1003 shown in FIG. 18, ligands 7 are provided only on metal layer 2, but may also be provided on metal layer 3, as shown in the sensor of Embodiment 1.

In addition, the plasmon sensor shown in FIG. 18 may be modified to have through-holes 25 provided in metal layer 3 similarly to the sensor according to Embodiment 1.

Exemplary Embodiment 3

Figure 19:
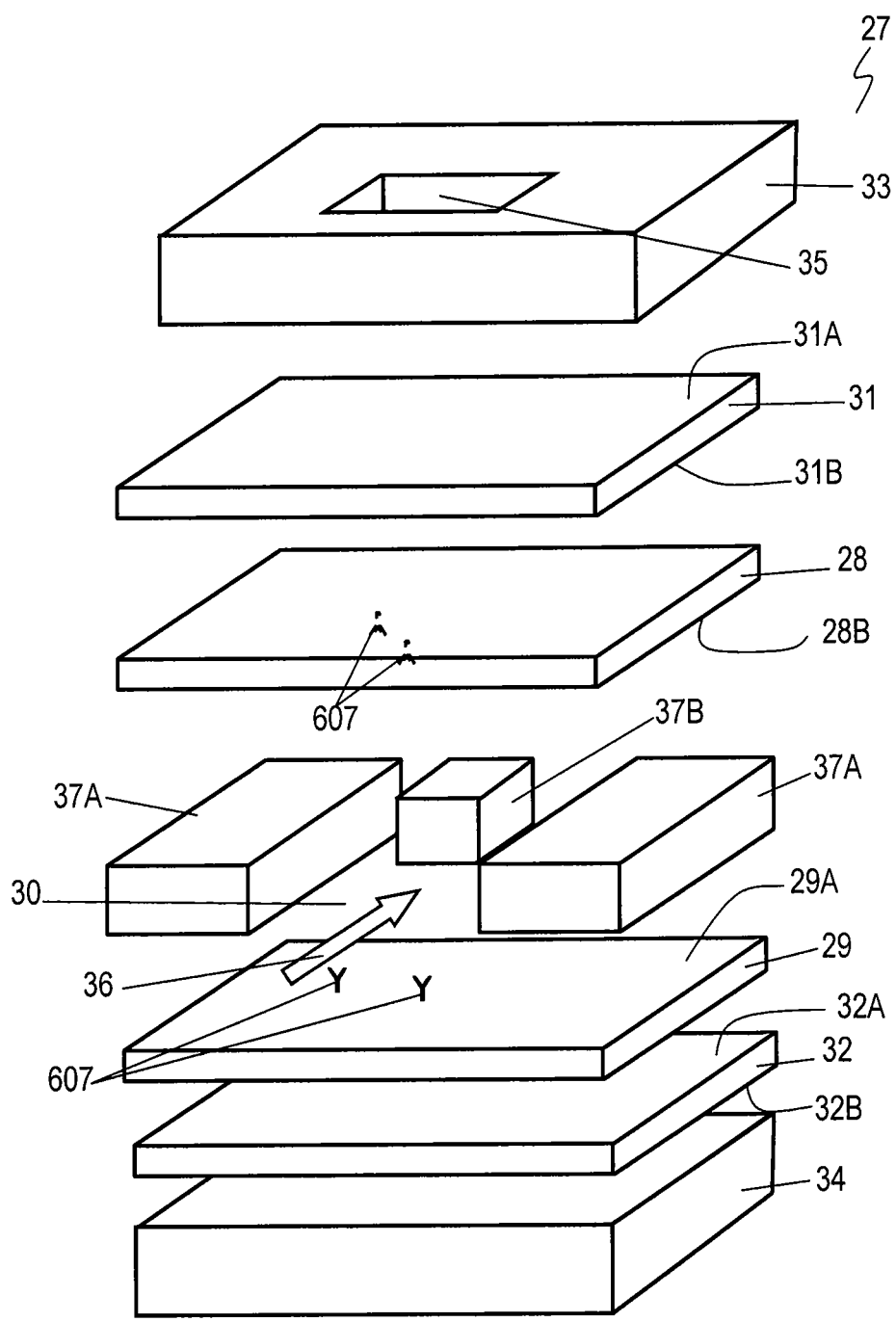
FIG. 19 is a perspective view of a plasmon sensor according to Exemplary Embodiment 3 of the invention.
Figure 20A:
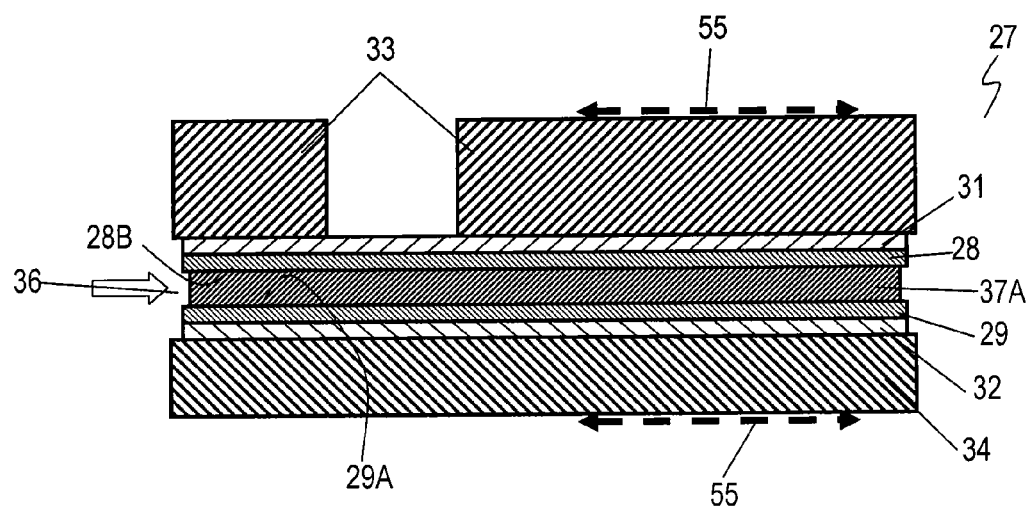
FIG. 20A is a side view of the plasmon sensor according to Embodiment 3.
Figure 20B:
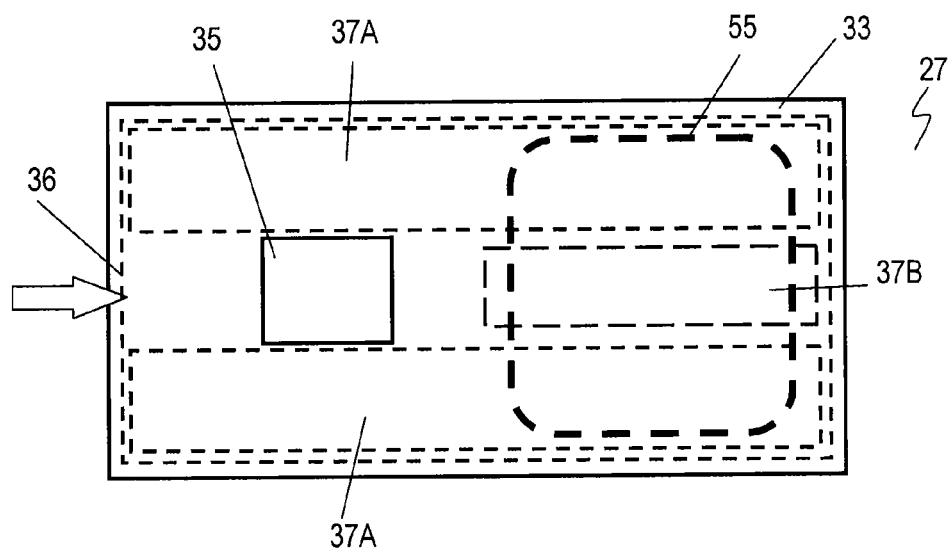
FIG. 20B is a top view of the plasmon sensor according to Embodiment 3.

FIGS. 19, 20A, and 20B are an exploded perspective view, a side view, and a top view of plasmon sensor 27 according to Embodiment 3, respectively. Plasmon sensor 27 includes metal layers 28 and 29, spacers 37A and 37B retaining metal layers 28 and 29 with a space of a predetermined distance between metal layers 28 and 29, supporter 31 for maintaining the shape of metal layer 28, and supporter 32 for maintaining the shape of metal layer 29. Plasmon sensor 27 has hollow space 30 between metal layers 28 and 29 other than the area occupied by spacers 37A and 37B. Each of metal layers 28 and 29, spacers 37A and 37B, supporters 31 and 32 and hollow space 30 has the same configuration as metal layers 2 and 3, spacers (walls 10 or posts 11), supporters 5 and 6 and hollow spaces 4 according to the previous embodiments. Lower surface 28B of metal layer 28 faces upper surface 29A of metal layer 29, so that hollow space 30 is formed between lower surface 28B of metal layer 28 and upper surface 29A of metal layer 29. Metal layer 28 is fixed onto lower surface 31B of supporter 31. Metal layer 29 is fixed onto upper surface 32A of supporter 32. Plasmon sensor 27 further includes resin piece 33 placed on upper surface 31A of supporter 31, resin piece 34 placed on lower surface 32B of supporter 32, aperture 35 formed in resin piece 33, and sample injection port 36 for injecting, into hollow space 30, a test sample containing an analyte. Plasmon sensor 27 includes ligands 607 disposed on at least one of the surfaces of metal layer 28 and 29 adjoining hollow space 30.

Supporter 31 is made of a thin film of low-loss optical glass having a thickness of, e.g. 200 μm in order to allow the incoming electromagnetic wave to efficiently pass through. As a result, plasmon sensor 27 shown in FIGS. 19, 20A, and 20B has the functions identical to those of the plasmon sensors shown from FIGS. 11A to 12B.

Supporter 31 is made of a thin film made of a low-loss optical glass having a thickness of about 200 μm to allow the electromagnetic wave entering from above resin piece 33 through aperture 35 penetrate efficiently therethrough. In this case, supporter 31 has sharp edges due to the optical glass having such a thickness. To prevent a user handling plasmon sensor 27 from getting injured by touching the edges of supporter 31, resin piece 33 has a size such that the edges of the resin piece extend beyond the edges of supporter 31, as shown in FIG. 20B. This structure allows a user to use plasmon sensor 27 safely.

The edges of resin piece 34 may extend beyond the edges of supporter 32, thereby providing the same effect.

Resin pieces 33 and 34 function as reinforcement plates, and prevent plasmon sensor 27 from getting damaged even if the user pinching plasmon sensor 27 with fingers. In addition, areas 55 may be provide as portions to be held by the user to hold plasmon sensor 27 with fingers, as shown in FIGS. 20A and 20B. In this case, spacer 37B may be placed between areas 55 of both resin pieces 33 and 34. Spacer 37B prevents hollow space 30 from deforming even when the user pinches and holds plasmon sensor 27 with fingers. This structure prevents plasmon sensor 27 from changing the resonance frequency of the surface plasmon resonance even when the user holds it with fingers while in use. Plasmon sensor 27 does not necessarily include spacer 37B, providing the same effects as those of Embodiments 1 and 2 even if spacer 37B is not provided.

The user uses plasmon sensor 27 by irradiating electromagnetic wave from above aperture 35 provided in resin piece 33. For example, the user causes the sunlight to irradiate through aperture 35, and visually observe the presence or absence of the specific binding between the ligands and analyte based on color of light reflected from aperture 35.

The user injects the analyte from sample injection port 36 into hollow space 30. If the electromagnetic wave to be irradiated is visible light, for instance, a space between metal layers 28 and 29 around sample injection port 36 is small since the spatial distance between metal layers 28 and 29 is small, ranging from about 300 nm to 1.0 mm. This distance allows the test sample to enter into hollow space 30 by a capillary phenomenon attributed to adhesiveness and surface tension of the test sample of liquid containing analyte. As a result, the user can easily inject the analyte into hollow space 30. The spatial distance between metal layers 28 and 29 around sample injection port 36 is chosen to be the size that enables the test sample to enter into hollow space 4 by the capillary phenomenon. Although sample injection port 36 is provided at one side of plasmon sensor 27, sample injection port 36 may be replaced by a through-hole penetrating through metal layer 3, resin piece 34 and supporter 32, so that the test sample can be injected into hollow space 30 similarly to the plasmon sensor shown in FIG. 16.

Figure 21:
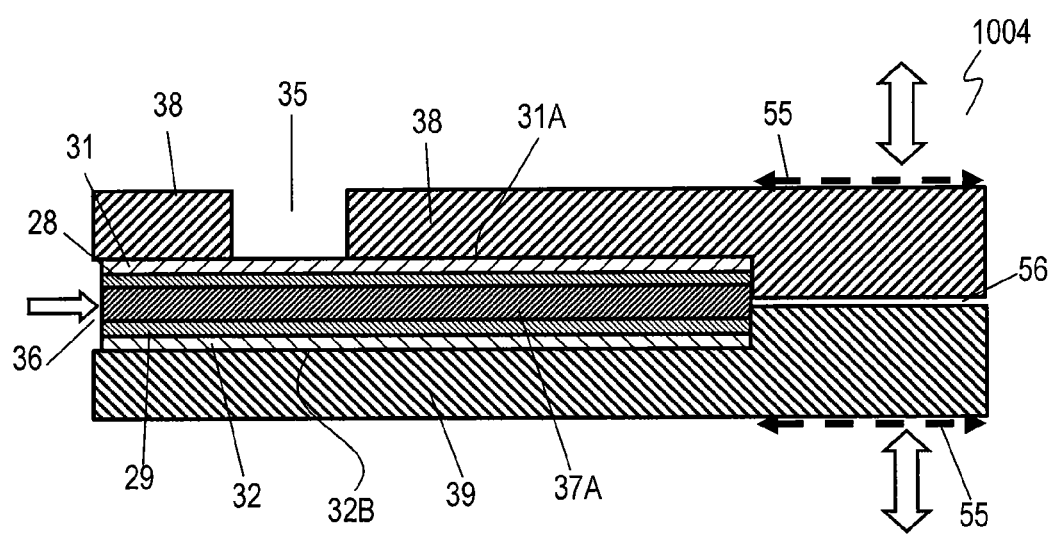
FIG. 21 is a side view of another plasmon sensor according to Embodiment 3.

FIG. 21 is a cross-sectional view of another plasmon sensor 1004 according to Embodiment 3. In FIG. 21, components identical to those of plasmon sensor 27 shown in FIGS. 19, 20A, and 20B are denoted by the same reference numerals. Plasmon sensor 1004 includes resin pieces 38 and 39 instead of resin pieces 33 and 34 shown in FIGS. 19, 20A and 20B, and does not include spacer 37B. Resin piece 38 is placed on upper surface 31A of supporter 31 similarly to resin piece 33 shown in FIG. 20A. Resin piece 38 has aperture 35 to expose upper surface 31A of supporter 31. Resin piece 39 is placed on lower surface 32B of supporter 32 similarly to resin piece 34 shown in FIG. 20A. Resin pieces 38 and 39 have areas 55 near one end opposite to sample injection port 36. Areas 55 are designated as portions where the user is directed to hold with fingers. In areas 55, resin pieces 38 and 39 faces each other across hollow space 56 communicating with hollow space 30. In other words, supporters 31 and 32, spacer 37A and metal layers 28 and 29 located behind areas 55 are not located between resin pieces 38 and 39 so that both movable resin pieces 38 and 39 directly faces hollow space 56.

The user can change a volume of hollow space 56 by pinching areas 55 hardly or softly with fingers. Such a manipulation can enhance the effect of capillary phenomenon to inject the test sample containing analyte into hollow space 56 through sample injection port 36. Short and quick changes of the volume of hollow space 56 causes the analyte to be stirred inside hollow space 56, and increases the speed of reaction between the analyte and the ligands.

In plasmon sensor 1004 shown in FIG. 21, supporters 31 and 32, spacer 37A and metal layers 28 and 29 are not provided behind areas 55 between movable resin pieces 38 and 39, but this structure is not restrictive. Similar advantages as discussed above can be achieved even with a structure having at least one of supporters 31 and 32, spacer 37A and metal layers 28 and 29 is partly located behind areas 55 between movable resin pieces 38 and 39.

The user can easily check at his/her home as to whether a testee is infected with influenza, for instance, when an antibody of influenza virus is used as ligands 607 in plasmon sensors 27 and 1004 according to Embodiment 3. In this case, the user collects body fluid, such as mucous membrane of the testee's nose, and prepares a test sample by dissolving the body fluid in a solution. Sample injection port 36 of one of plasmon sensors 27 and 1004 according to Embodiment 3 is dipped in this test sample to allow the test sample to enter into hollow space 56 by the capillary phenomenon, and causes the test sample to contact the ligands.

In plasmon sensors 27 and 1004 shown in FIGS. 19 to 21, the position of sample injection port 36 are not limited to that specified in FIGS. 19 to 21, and can be located to any place as appropriate with consideration given to the convenience of use by the user. In this connection, the shapes and positions of spacers 37A and 37B can also be optimized as required. Particularly in plasmon sensor 1001 shown in FIGS. 12A and 12B, hollow space 4 between metal layers 2 and 3 other than the area occupied by posts 11 opens at all side areas of metal layers 2 and 3 without being blocked by posts 11, so that all side areas of metal layers 2 and 3 can be used as sample injection ports 36.

Figure 22:
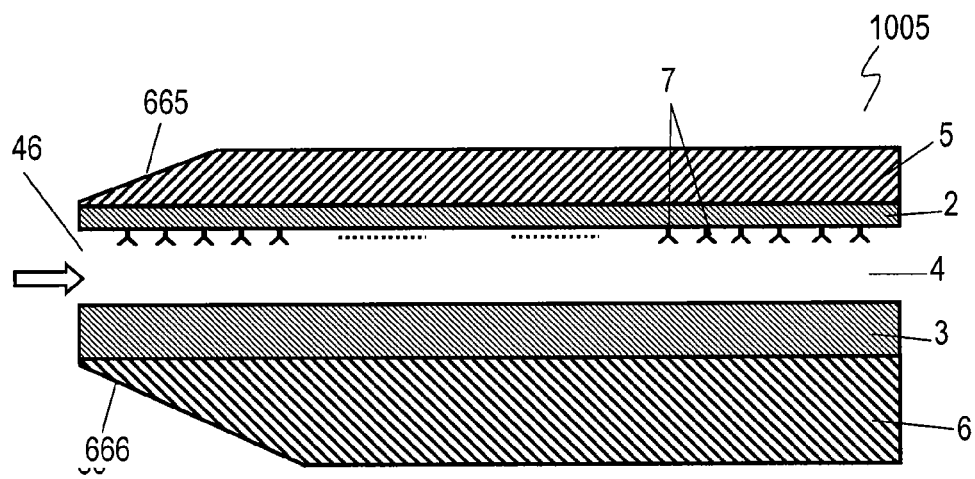
FIG. 22 is a side view of still another plasmon sensor according to Embodiment 3.

This shape of sample injection ports 36 can be protected from being clogged by impurities in the test sample. FIG. 22 is a cross-sectional view of still another plasmon sensor 1005 according to Embodiment 3. In FIG. 22, components identical to those of plasmon sensor 1 shown in FIG. 1 are denoted by the same reference numerals. In plasmon sensor 1005, supporters 5 and 6 have tapered portions 665 and 666 tapered toward sample injection port 46 at respective one ends thereof.

When the test sample is injected into hollow space 4 through sample injection port 46 by the capillary phenomenon, impurities contained in the test sample may have a size larger than that of sample injection port 46 and block a part of sample injection port 46, hence decreasing an efficiency of injecting the test sample into hollow space 4. However, tapered portions 665 and 666 provided near sample injection port 46 prevents the impurities from staying around sample injection port 46, and reduces a risk of decreasing the injection efficiency of the test sample into hollow space 4.

Exemplary Embodiment 4

Figure 23:
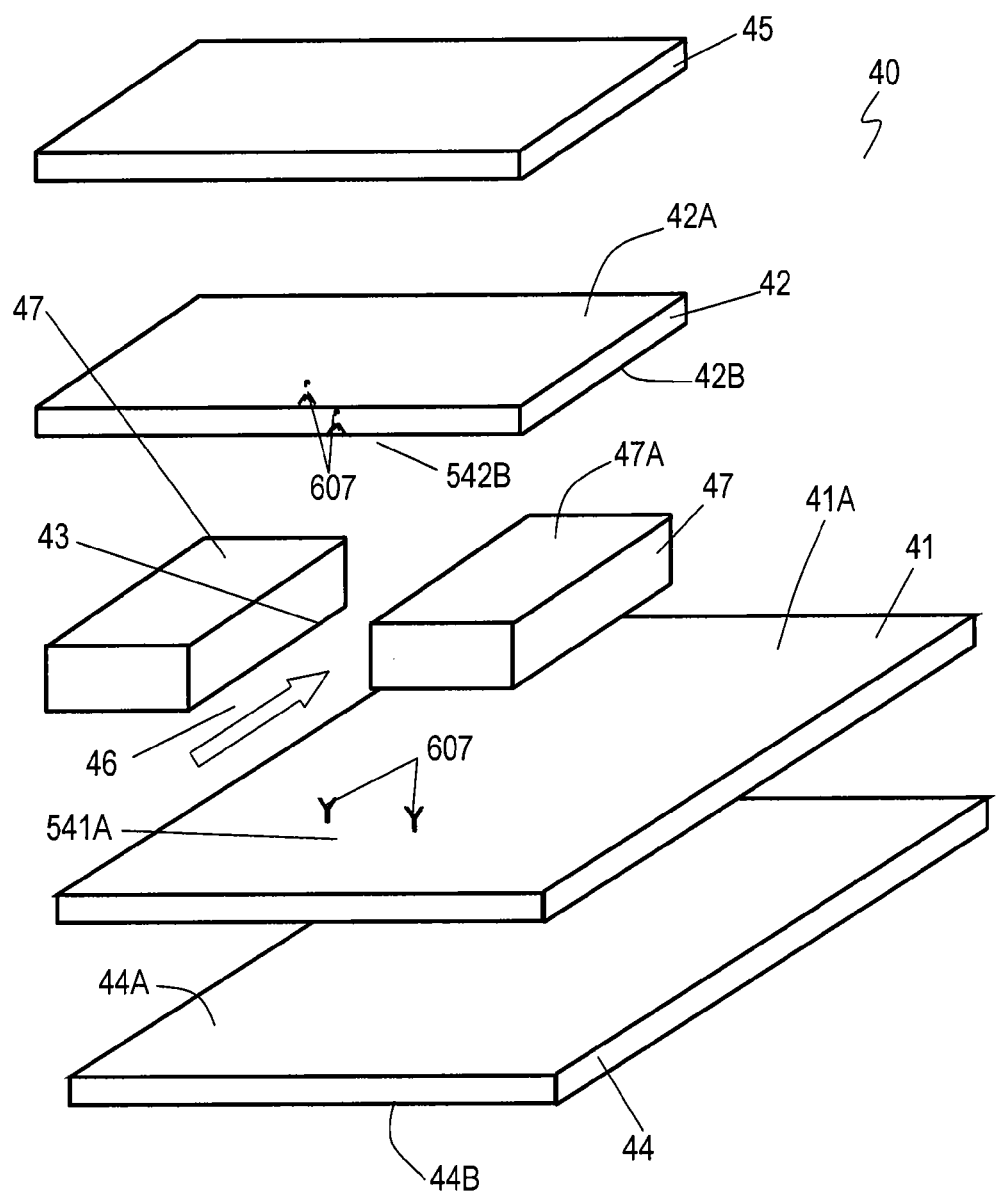
FIG. 23 is an exploded perspective view of a plasmon sensor according to Exemplary Embodiment 4 of the invention.

FIG. 23 is an exploded perspective view of plasmon sensor 40 according to Exemplary Embodiment 4. Plasmon sensor 40 includes supporter 44, metal layer 41 placed on upper surface 44A of supporter 44, spacers 47 placed on upper surface 41A of metal layer 41, metal layer 42 placed on upper surfaces 47A of spacers 47, and supporter 45 placed on upper surface 42A of metal layer 42. Hollow space 43 is provided in an area between metal layers 41 and 42 except for the area occupied by spacers 47. Plasmon sensor 40 further includes sample injection port 46 for injecting a test sample into hollow space 43. Ligands 607 are formed on at least one of upper surface 41A of metal layer 41 facing hollow space 43 and lower surface 43B of metal layer 42 facing hollow space 43. Supporters 44 and 45, metal layers 41 and 42, and spacers 47 are made of the same materials as supporters 32 and 31, metal layers 29 and 28, and spacers 37A shown in FIG. 19.

In plasmon sensor 40, supporter 44 has a size larger than that of supporter 45, or metal layer 41 has a size larger than that of metal layer 42.

Supporter 44 is made of a thin film of low-loss optical glass having a thickness of, e.g. 200 μm in order to allow the incoming electromagnetic wave to efficiently pass through. As a result, plasmon sensor 40 shown in FIG. 23 can have functions similar to plasmon sensor 27 shown in FIG. 19.

Figure 24:
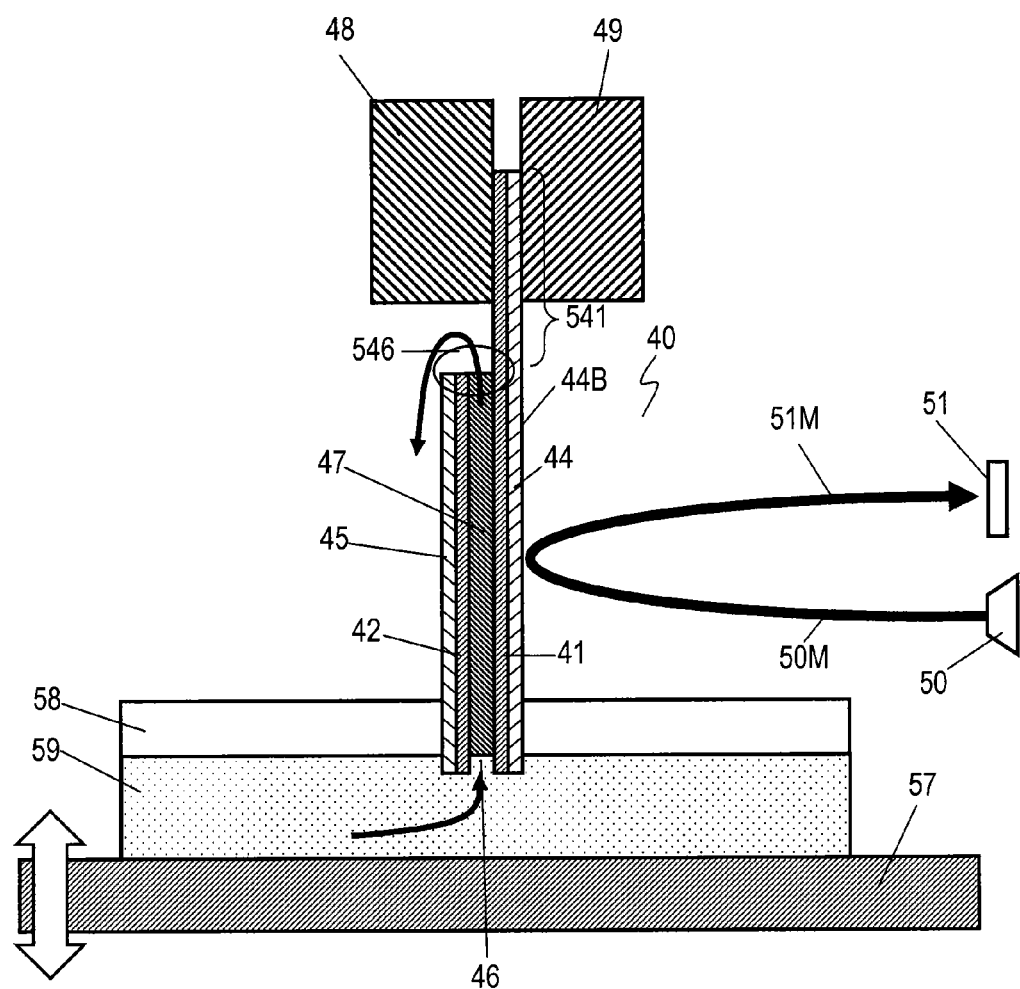
FIG. 24 is a side view of the plasmon sensor according to Embodiment 4 for illustrating a method of using the plasmon sensor.

A method of using plasmon sensor 40 will be described below. FIG. 24 is a side view of plasmon sensor 40 for illustrating the method of using the sensor. Light source 50 irradiates light 50M, an electromagnetic wave, to supporter 44. Detector unit 51 receives and detects light 51M reflected from plasmon sensor 40. Metal layer 41 and supporter 44 have a size larger than that of metal layer 42 and supporter 45. Plasmon sensor 40 is fixed by having sensor holding portion 541, which is portions of metal layer 41 and supporter 44 not facing metal layer 42 and supporter 45, placed between resin pieces 48 and 49. This structure prevents a spatial distance between metal layers 41 and 42 from changing less than the sensor of pinching supporters 44 and 45 to hold plasmon sensor 40, thereby reducing a variation in resonant wavelength of the surface plasmon resonance.

Sample injection port 46 for receiving injection of the test sample in a liquid form containing analyte is located near a lower end of plasmon sensor 40 when plasmon sensor 40 is fixed between resin pieces 48 and 49.

Container 58 provided on movable stage 57 is located under plasmon sensor 40 when plasmon sensor 40 is fixed with resin pieces 48 and 49, as shown in FIG. 24. Container 58 is filled with test sample 59 of liquid containing analyte.

Test sample 59 injected from sample injection port 46 moves inside hollow space 43 of plasmon sensor 40, and is discharged from area 546 opposite to sample injection port 46. This configuration can prevent surface 44B of supporter 44 facing light source 50 and detector unit 51 from being stained with test sample 59 so as avoid to test sample 59 from obstructing the electromagnetic wave entering supporter 44, and maintain an excellent measuring condition.

Plasmon sensor 40 is fixed with resin pieces 48 and 49, and container 58 filled with the test sample containing analyte can be placed on movable stage 57. Sample injection port 46 is dipped in test sample 59 by moving movable stage 57 vertically to cause test sample 59 to enter into hollow space 43 by the capillary phenomenon.

Since the analyte can be introduced while plasmon sensor 40 is held securely with resin pieces 48 and 49, the light from light source 50 can be irradiated on the same position at any time, thereby enabling detector unit 51 to monitor a reflective characteristic of the same position. Accordingly, plasmon sensor 40 according to Embodiment 4 can measure changes of speed of the reaction between the analyte and the ligands and the resonant wavelength continuously and accurately.

In FIG. 24, container 58 may be replaced with a slide glass carrying several drops of test sample 59 containing the analyte.

An atmospheric pressure in the space where plasmon sensor 40 and container 58 are disposed can be changed with time to facilitate the stirring of the test sample entered in hollow space 43 in order to accelerate the speed of the reaction between the analyte in the test sample and metal layer 41 or ligands 607 provided on metal layer 41. Since test sample 59 is introduced into hollow space 43 by the capillary phenomenon with using the atmospheric pressure applied to the surface of the test sample, the test sample is stirred as the test sample moves within hollow space 43 in responsive to the change of the atmospheric pressure with time.

A convective flow of test sample 59 of liquid may be preferably produced by raising a temperature of test sample 59 in order to accelerate the speed of the reaction between ligands 607 and the analyte in test sample 59. A flow of test sample 59 may preferably produced by applying an electric field or a magnetic field of a frequency different from that of the electromagnetic wave irradiated from light source 50.

In FIGS. 23 and 24, resin pieces 48 and 49 are fixed to respective one ends of supporter 44 and metal layer 41, this is not restrictive. Any of supporter 45 and metal layer 42 may have a size larger than that of supporter 44 and metal layer 41. Resin pieces 48 and 49 may be fixed to one end of at least one of supporter 45 and metal layer 42, still providing the same effects.

In FIG. 24, sample injection port 46 is dipped into test sample 59 by moving movable stage 57 vertically, this is not restrictive. Resin pieces 48 and 49 can be moved vertically to provide the same effect.

An absorbent material for absorbing test sample 59 may be provided in area 546 shown in FIG. 24. The absorbent material sucks up test sample 59 from inside of hollow space 43 and increases the moving speed of test sample 59 into hollow space 43, thereby increasing the speed of reaction between the ligands and the analyte.

Ligands 607 can be provided on any of surface 41A of metal layer 41 and surface 42B of metal layer 42 by the following method. After a test sample containing ligands is injected into hollow space 43 through sample injection port 46 by the capillary phenomenon, the test sample containing the ligands is dried. Ligands 607 can be disposed in this way on at least one of adjacent region 541A around surface 41A of metal layer 41 and adjacent region 542A around surface 42B of metal layer 42. This method enables ligands 607 to be fixed after plasmon sensor 40 is assembled. In plasmon sensor 1 shown in FIGS. 11A and 11B, this method can improve the strength of bonding between walls 10 and metal layer 3 when gold-to-gold bonding is used to bond walls 10 to metal layer 3. In this case, when ligands 7 are fixed to surfaces 2B and 3A of metal layers 2 and 3 before walls 10 and metal layer 3 are bonded by gold-to-gold bonding, for example, ligands 7 are likely to move between walls 10 and metal layer 3, hence decreasing the adhesion between walls 10 and metal layer 3. However, such a decrease in the adhesion between walls 10 and metal layer 3 can be avoided by fixing ligands 7 to surfaces 2B and 3A after plasmon sensor 1 is assembled similarly to plasmon sensor 40.

Exemplary Embodiment 5

Figure 25:
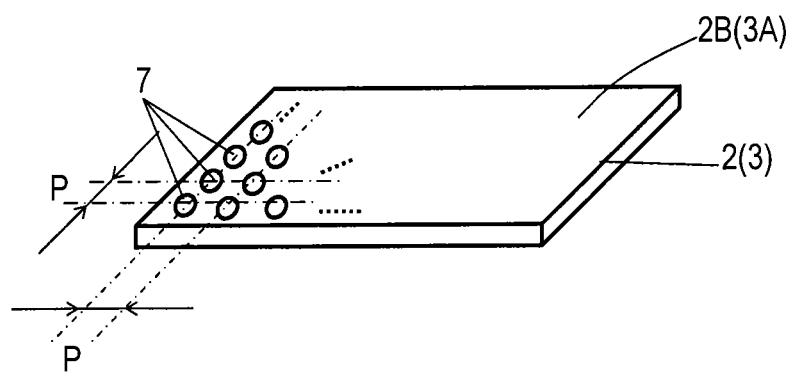
FIG. 25 is a schematic view of a plasmon sensor according to Exemplary Embodiment 5 of the invention.

FIG. 25 is a perspective view of metal layer 2 (3) according to Embodiment 5. In FIG. 25, components identical to those of plasmon sensor 1 shown in FIG. 1 are denoted by the same reference numerals. Metal layer 2 (3) shown in FIG. 25 has ligands 7 arranged in a matrix form on surface 2A (3B).

Pitch P between adjoining ligands 7 is larger than the wavelength of the electromagnetic wave supplied to metal layer 2 through a supporter but is smaller than 200 μm.

Conventional plasmon sensor 100 shown in FIG. 28 requires prism 101, and therefore, the light enters metal layer 102 at an angle inclining by a certain degree. Therefore, in conventional plasmon sensor 100 shown in FIG. 28, a plasmon wave propagates near the surface of metal layer 102. For this reason, the individual ligands 104 are required to be spaced by pitches larger than a propagating range of the plasmon wave, hence preventing ligands 104 from being arranged at a high density by narrow pitches if they are arranged in a matrix form on the surface of metal layer 102. If ligands 104 are arranged by pitches smaller than the propagating range of the plasmon wave, mutual interference can occur and prevent an accurate measurement. In conventional plasmon sensor 100 shown in FIG. 28, for this reason, the ligands are arranged at regular pitches larger than 200 μm even if they are arranged in the matrix form.

On the other hand, the plasmon sensors according to Embodiments 1 to 5 of the invention do not cause the plasmon wave to propagate since they introduce the electromagnetic wave to enter vertically to metal layer 2 (3). This structure provides an accurate measurement result without causing the mutual interference even if ligands 7 are arranged in a matrix form by pitches reduced to a distance of the wavelength of the electromagnetic wave entering from the outside. This can increase the number of the ligands per unit area, and provides various types of sensing.

According to Embodiments 1 to 4, ligands 7 can be arranged in the matrix form not only on metal layers 2, 28 and 41 but also on metal layers 3, 29 and 42 to increase the detecting sensitivity of the plasmon sensor. In this configuration, the ligands provided on metal layers 3, 29 and 42 may face vertically the ligands provided on metal layers 2, 28 and 41, further increasing the detecting sensitivity of the plasmon sensor.

According to Embodiment 5, a CCD camera may be used for detecting electromagnetic waves reflected from the plasmon sensor. This camera can collectively and accurately detect the electromagnetic waves reflected from any of metal layers 2, 28 and 41 near the ligands arranged in the matrix form. The reflected eave can detected easily at high sensitivity even in the configuration having the ligands arranged in the matrix form at small pitches.

Ligands 7 arranged in the matrix form can include plural kinds of ligands, thus allowing plasmon sensor 1 to detect plural kinds of analyte in the test sample with a single plasmon sensor.

Exemplary Embodiment 6

Figure 26:
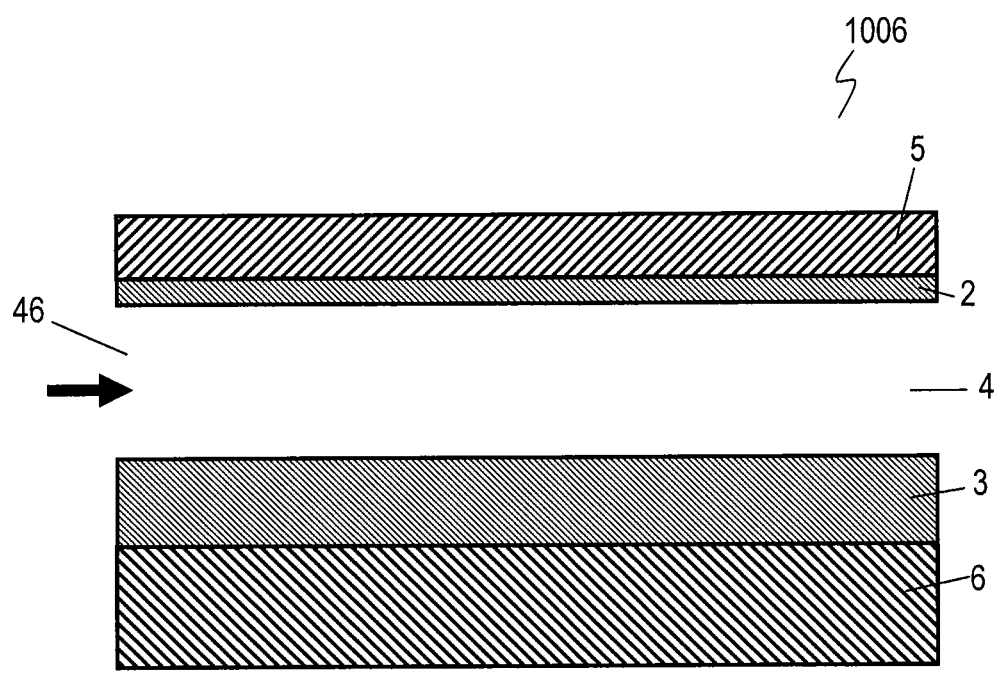
FIG. 26 is a cross-sectional view of plasmon sensor 1006 according to Exemplary Embodiment 6 of the invention.

FIG. 26 is a cross-sectional view of plasmon sensor 1006 according to Embodiment 6 of the present invention. In FIG. 26, components identical to those of plasmon sensor 1 shown in FIG. 1 are denoted by the same reference numerals. Plasmon sensor 1006 of Embodiment 6 does not include ligands 7 on lower surface 2B of metal layer 2 adjoining hollow space 4. More specifically, plasmon sensor 1006 includes metal layer 2 situated on lower surface 5B of supporter 5, and metal layer 3 placed below metal layer 2 facing lower surface 2B of metal layer 2. Hollow space 4 is provided in at least a part of the space between metal layers 2 and 3. An electromagnetic wave is irradiated to metal layer 2 from above upper surface 2A of metal layer 2.

A mixture fluid of test sample and ligands is injected from sample injection port 46 of plasmon sensor 1006. Hollow space 4 is filled with the mixture fluid of the test sample and the ligands, according to Embodiment 6.

The test sample and the ligands may be mixed outside of plasmon sensor 1 before injecting them into plasmon sensor 1. The test sample and ligands may be injected into hollow space 4 separately, and mixed in hollow space 4.

If an analyte exists in the test sample, a specific binding performed between the analyte in the test sample and the ligands when the test sample and the ligands are mixed.

After the specific binding, a relative dielectric constant changes to a different value from that of the analyte and the ligands when they are separated. This is attributed to the fact that a molecular structure of the specifically bound analyte and ligand becomes different from the molecular structures of the analyte and the ligand when they are separated. For this reason, the resonant wavelength of plasmon sensor 1006 becomes different when the test sample contains analyte and not contains analyte. Accordingly, plasmon sensor 1006 has a structure not provided with ligands 7 on any of the surfaces of metal layer 2 and metal layer 3, yet can detect the presence or absence of specific binding between the ligands and analyte. The structure of plasmon sensor 1006 according to Embodiment 6 can hence avoid the time-consuming process of disposing ligands 7 necessary in plasmon sensor 1, thereby providing plasmon sensor 1006 with high productivity.

Figure 27:
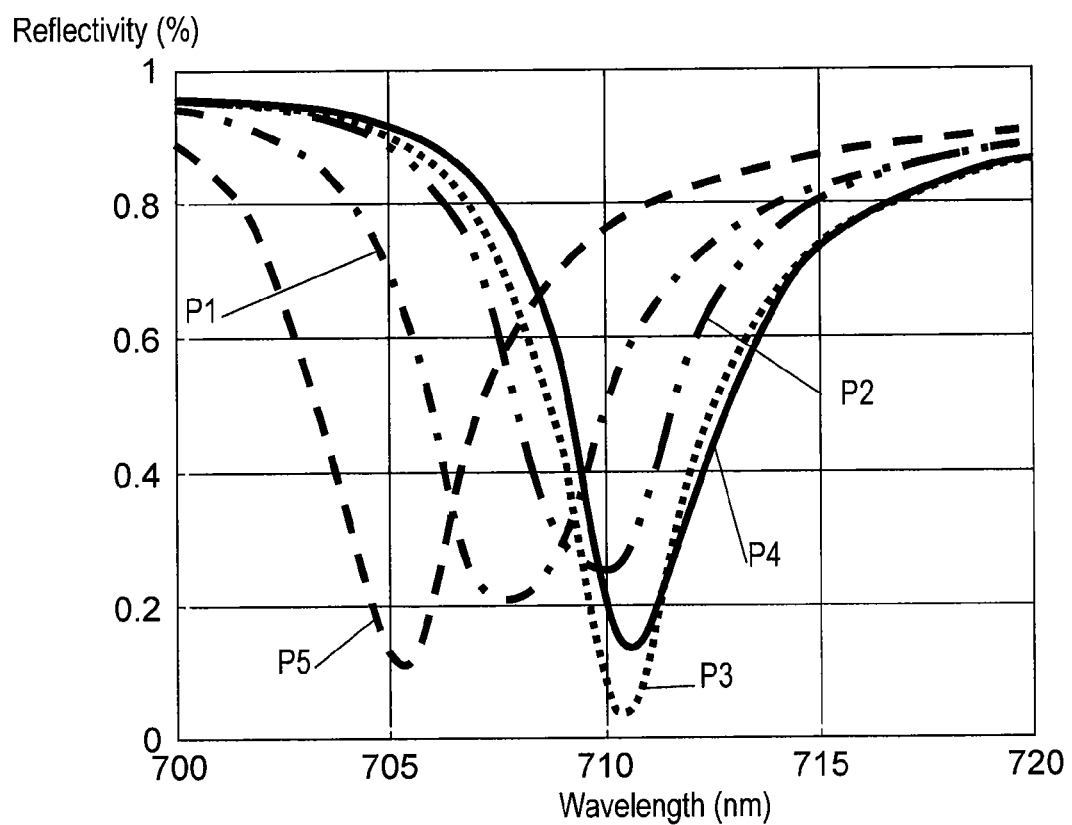
FIG. 27 shows an analysis result of an electromagnetic field simulation on an analysis model of the plasmon sensor according to Embodiment 6.

FIG. 27 shows an analysis result of an electromagnetic field simulation on an analysis model of plasmon sensor 1006. The changes in the resonant wavelength with molecules having the structure existing in hollow space 4 after specific binding between ligands and analyte (modeled in a layer having relative dielectric constant of 1.1 and thickness of 100 nm), and more specifically to the relationship between the locations of the molecules of specifically bound structure inside hollow space 4 and the corresponding resonant wavelength. The analysis model has the following properties:

Metal layer 2: a gold layer having a thickness of 45 nm;
Metal layer 3: a gold layer having a thickness of 300 nm;
Spatial distance between metal layers 2 and 3: 1 μm (a layer of air); and
Incidence angle of light: perpendicular to surface 2A of metal layer 2.

All results of the simulation analyses performed in the present application are obtained with the MW-studio made by Computer Simulation Technology AG as an analytical tool.

Reflectivity P5 shown in FIG. 27 represents the reflectivity when molecules of the specifically bound structure between ligands and analyte do not exist in hollow space 4, and the resonant wavelength is 705.4 nm. Reflectivities P1 and P2 represent the reflectivities when the molecules of the specifically bound structure exist on surface 2B of metal layer 2 and surface 3A of metal layer 3 respectively, and the resonant wavelength is 707.1 nm. Reflectivities P3 and P4 represent the reflectivities when the molecules of the specifically bound structure exist on both surfaces 2B and 3A of metal layers 2 and 3 adjoining hollow space 4, and when the molecules exist in the intermediate area between metal layers 2 and 3, respectively, and the resonant wavelength of plasmon sensor 1006 is 710.4 nm. As shown, the resonant wavelength of plasmon sensor 1006 changes even when the molecules of the specifically bound structure of the ligands and the analyte exist in any area other than surfaces 2B and 3A of metal layers 2 and 3. In other words, plasmon sensor 1006 can recognize the presence or absence of the specific binding between the ligands and the analyte even if the ligands are not disposed on the surfaces of metal layers 2 and 3, and the mixture fluid of the test sample and the ligands is prepared outside of plasmon sensor 1 prior to injection into hollow space 4.

In plasmon sensor 1006 according to Embodiment 6, ligands 7 are not provided on any of surfaces 2B and 3A of metal layers 2 and 3, that is, no ligand 7 is provided on the inner walls of hollow space 4. However, ligands 7 may be provided on any of the surfaces of metal layer 2 and metal layer 3. In other words, a mixture fluid of the test sample and ligands 7 is disposed into hollow space 4 of plasmon sensor 1 shown in FIG. 1 according to Embodiment 1. In this case, the analyte contained in the test sample but not specifically bound with ligands 7 performs to specifically bind with ligands 7 disposed on any of the surfaces of metal layer 2 and 3, and causes a change in the resonant wavelength, thereby further increasing sensitivity of the sensor for detecting the presence of the specific binding. In this alternative, an amount of ligands 7 may be reduced in relation to the analyte when used outside of hollow space 4 for mixing with the test sample. This allows some of the analyte to remain in the mixture fluid of the test sample and ligands 7, and perform specific bind with ligands 7 disposed on any of the surfaces of metal layers 2 and 3 after the mixture fluid is injected into hollow space 4.

According to Embodiments 1 to 6, supporter 5 is provided above metal layer 2, this is not restrictive. Supporter 5 can be provided under metal layer 2. When supporter 5 is provided under metal layer 2, ligands 7 are provided on the lower surface of supporter 5. If supporter 5 has a high relative dielectric constant, the resonant wavelength can be longer, accordingly reducing a cost of the electromagnetic wave source since a frequency of the electromagnetic wave supplied from above metal layer 2 can be lowered.

All of metal layer 2, supporter 5, metal layer 3, and supporter 6 have flat shapes according to Embodiments 1 to 6, and not restrictive. They can have rough surfaces, providing the same effects. Accordingly, the plasmon sensor can exert its functions without problems even if they bear small asperities on the surfaces in the process of manufacturing.

In the above description, the visible light is used as the electromagnetic wave. However, the electromagnetic wave may have other wavelength than the visible light, providing the same effects.

According to Embodiments 1 to 6, terms, such as "upper surface", "lower surface", "above" and "under", indicating directions merely indicate relative directions dependent only upon relative positions of components of the plasmon sensors, and do not indicate absolute directions, such as a vertical direction.

INDUSTRIAL APPLICABILITY

A plasmon sensor according to the present invention has a small size and a simple structure, and is useful for, e.g. an inexpensive biosensor.

REFERENCE MARKS IN THE DRAWINGS

2 Metal Layer (First Metal Layer)
3 Metal Layer (Second Metal Layer)
4 Hollow Space
5 Supporter (First Supporter)
6 Supporter (Second Supporter)
7 Ligand
8 Analyte
10 Wall (Spacer)
11 Post (Spacer)
12 Sample Injection Port
22 Electrode
25 Through-Hole
26 Movable Stage (Adjusting Mechanism)
28 Metal Layer (First Metal Layer)
29 Metal Layer (Second Metal Layer)
30 Hollow Space
31 Supporter (First Supporter)

32 Supporter (Second Supporter)
37 Spacer
41 Metal Layer (First Metal Layer)
42 Metal Layer (Second Metal Layer)
43 Hollow Space
44 Supporter
45 Supporter
46 Sample Injection Port
47 Spacer
665 Tapered Portion
666 Tapered Portion

The invention claimed is:

1. A plasmon sensor comprising:
a first metal layer made of a metal having an upper surface and a lower surface;
a second metal layer having an upper surface and a lower surface, the upper surface of the second metal layer facing the lower surface of the first metal layer;
a spacer maintaining a constant distance between the lower surface of the first metal layer and the upper surface of the second metal layer;
a first supporter provided on the upper surface of the first metal layer, and,
a second supporter provided on the lower surface of the second metal layer,
wherein a hollow space is provided between the lower surface of the first metal layer and the upper surface of the second metal layer,
wherein the metal of the first metal layer and the first supporter are configured to allow an electromagnetic wave to pass through, and
wherein a thickness of the second metal layer is larger than a thickness of the first metal layer.

2. The plasmon sensor according to claim 1, wherein a plurality of antibodies are configured to be disposed on at least one of a first adjacent region around the first metal layer and a second adjacent region around the second metal layer.

3. The plasmon sensor according to claim 2,
wherein the hollow space is configured to be filled with a test sample containing a medium, and
wherein the hollow space is configured to have a mixed fluid containing the test sample and the plurality of antibodies injected therein.

4. The plasmon sensor according to claim 1, wherein the second metal layer has a through-hole formed therein.

5. The plasmon sensor according to claim 1,
wherein the hollow space is configured to be filled with a test sample containing a medium, and
wherein a state of the medium inside the hollow space is changed with time.

6. The plasmon sensor according to claim 5, wherein a wavelength for generating a surface plasmon resonance changes from an invisible light range to a visible light range or from the visible light range to the invisible light range by changing the state of the medium inside the hollow space with time.

7. The plasmon sensor according to claim 5, wherein a wavelength for generating surface plasmon resonance changes from an invisible light range to one of a range between 450 nm and 570 nm and a range between 620 nm and 750 nm, or changes from one of a range between 450 nm and 570 nm and a range between 620 nm and 750 nm to the invisible light range by changing the state of the medium inside the hollow space with time.

8. The plasmon sensor according to claim 5, wherein a wavelength for generating surface plasmon resonance changes from a range between 450 nm and 495 nm to a range between 495 nm and 580 nm by changing the state of the medium inside the hollow space with time.

9. The plasmon sensor according to claim 5,
wherein a plurality of antibodies are disposed on at least one of a first adjacent region around the first metal layer and a second adjacent region around the second metal layer,
wherein the plurality of antibodies are arranged in a matrix form at regular pitches in at least one of the first adjacent region and the second adjacent region, and
wherein the pitches is larger than a wavelength of the electromagnetic wave and smaller than 200 μm.

10. The plasmon sensor according to claim 5,
wherein a test sample containing no analyte has refractive index n,
wherein electromagnetic field intensity distribution of an m-th order mode is produced between the first metal layer and the second metal layer before the test sample containing no analyte is placed in the hollow space, and
wherein the plasmon sensor satisfies a relation:
$m=a/(n-1)$, where a is an integer not smaller than 1.

11. The plasmon sensor according to claim 5,
wherein a wavelength for generating surface plasmon resonance changes within a predetermined wavelength range when a state of the hollow space changes from not being filled with a test sample containing no analyte to being filled with the test sample containing no analyte, and
wherein the predetermined wavelength range is one of a wavelength range between 380 nm and 450 nm, a wavelength range between 450 nm and 495 nm, a wavelength range between 495 nm and 570 nm, a wavelength range between 570 nm and 590 nm, a wavelength range between 590 nm and 620 nm, and a wavelength range between 620 nm and 750 nm.

12. The plasmon sensor according to claim 5, wherein, when a state of the medium inside the hollow space is changed with time, a wavelength for generating surface plasmon resonance changes from one of a wavelength range between 380 nm and 450 nm, a wavelength range between 450 nm and 495 nm, a wavelength range between 495 nm and 570 nm, a wavelength range between 570 nm and 590 nm, a wavelength range between 590 nm and 620 nm, and a wavelength range between 620 nm and 750 nm to another wavelength range the wavelength range between 380 nm and 450 nm, the wavelength range between 450 nm and 495 nm, the wavelength range between 495 nm and 570 nm, the wavelength range between 570 nm and 590 nm, the wavelength range between 590 nm and 620 nm, and the wavelength range between 620 nm and 750 nm.

13. The plasmon sensor according to claim 5, wherein, when a state of the medium inside the hollow space is changed with time, a wavelength for generating surface plasmon resonance changes from an invisible light range to one of a wavelength range between 380 nm and 450 nm, a wavelength range between 450 nm and 495 nm, a wavelength range between 495 nm and 570 nm, a wavelength range between 570 nm and 590 nm, a wavelength range between 590 nm and 620 nm, and a wavelength range between 620 nm and 750 nm.

14. The plasmon sensor according to claim 5, wherein, when a state of the medium inside the hollow space is changed with time, a wavelength for generating surface plasmon resonance changes to an invisible light range from one of a wavelength range between 380 nm and 450 nm, a wavelength range between 450 nm and 495 nm, a wavelength range between 495 nm and 570 nm, a wavelength range between 570 nm and 590 nm, a wavelength range between 590 nm and 620 nm, and a wavelength range between 620 nm and 750 nm.

15. The plasmon sensor according to claim 1, further comprising a sample injection port for injecting the test sample containing analyte into the hollow space.

16. The plasmon sensor according to claim 1,
wherein the spacer forms the hollow space in at least a part of space between the first metal layer and the second metal layer,
wherein a part or all of the spacer is made of material identical to material of at least one of the first metal layer and the second metal layer.

17. The plasmon sensor according to claim 16,
wherein the spacer includes a first layer and a second layer,
wherein the first layer is made of material identical to material of at least one of the first metal layer and the second metal layer, and
wherein the first layer has a thickness smaller than a thickness of the second layer.

18. The plasmon sensor according to claim 16, wherein the spacer is fixed with an end portion of the spacer inserted in at least one of the first metal layer and the second metal layer.

19. The plasmon sensor according to claim 1, wherein the test sample is injected into the hollow space by a capillary phenomenon.

20. The plasmon sensor according to claim 1, wherein:
the second supporter retains the second metal layer,
wherein the first supporter retains the first metal layer, and
wherein one of the first supporter and the second supporter constitutes a sensor holding portion.

21. The plasmon sensor according to claim 1, wherein the hollow space is filled with a compressed gas as the test sample.

22. The plasmon sensor according to claim 1,
wherein one end of at least one of the first supporter and the second supporter has a tapered portion.

23. The plasmon sensor according to claim 1, wherein the first metal layer has a thickness not larger than 100 nm.

24. The plasmon sensor according to claim 23, wherein the second metal layer has a thickness not smaller than 100 nm.

25. The plasmon sensor according to claim 1, wherein the second metal layer has a thickness not smaller than 100 nm.

26. The plasmon sensor according to claim 1, wherein electromagnetic field intensity of the electromagnetic wave entering in the hollow space is distributed between the first metal layer and the second metal layer in a high-order mode at a frequency for generating surface plasmon resonance.

27. The plasmon sensor according to claim 1,
wherein a thickness of the second supporter is larger than a thickness of the first supporter.

28. The plasmon sensor according to claim 1,
wherein the thickness of the second metal layer is larger than a thickness of both of the first metal layer and the first supporter.

29. The plasmon sensor according to claim 1,
wherein a thickness of the second supporter is larger than a thickness of both of the first metal layer and the first supporter.

30. The plasmon sensor according to claim 1,
wherein the distance between the first metal layer and the second metal layer is substantially equal to:

$$(1/2) \times \lambda \times m$$

where $\lambda$ is a wavelength of the electromagnetic wave entering in the space and m is an integer not smaller than one.

31. A plasmon sensor comprising:
a first metal layer having an upper surface and a lower surface which is configured to receive an electromagnetic wave, the electromagnetic wave being configured to pass through the first metal layer;
a second metal layer having an upper surface facing the lower surface of the first metal layer;
a spacer maintaining a constant distance between the lower surface of the first metal layer and the upper surface of the second metal layer; and
a first supporter provided on the upper surface of the first metal layer,
wherein a hollow space is provided between the lower surface of the first metal layer and the upper surface of the second metal layer, and
wherein the distance between the lower surface of the first metal layer and the upper surface of the second metal layer is substantially equal to:

$$(1/2) \times \lambda \times m$$

where $\lambda$ is a wavelength of the electromagnetic wave entering in the hollow space and m is an integer not smaller than one,
wherein the first supporter and the first metal layer are made of an optically transparent material for allowing the electromagnetic wave to pass through, and
wherein a thickness of the second metal layer is larger than a thickness of the first metal layer.

32. The plasmon sensor according to claim 31, wherein a plurality of antibodies are configured to be disposed on at least one of a first adjacent region around the lower surface of the first metal layer and a second adjacent region around the upper surface of the second metal layer.

33. The plasmon sensor according to claim 31, wherein the second metal layer has a through-hole formed therein.

34. The plasmon sensor according to claim 31, wherein an electromagnetic field intensity is distributed between the first metal layer and the second metal layer in a high-order mode at a frequency for generating surface plasmon resonance.

35. The plasmon sensor according to claim 31,
wherein the hollow space is configured to be filled with a test sample containing a medium, and
wherein a state of the medium inside the hollow space is changed with time.

36. The plasmon sensor according to claim 1, further comprising an alternating-current (AC) power source that applied an AC voltage between the first metal layer and the second metal layer.

37. The plasmon sensor according to claim 2, wherein the plurality of antibodies are configured to be disposed on at least one of the lower surface of the first metal layer and the upper surface of the second metal layer.

38. The plasmon sensor according to claim 2, wherein the spacer is disposed between the first metal layer and the second metal layer.

39. The plasmon sensor according to claim 2, wherein the spacer comprises a plurality of spacers disposed between the first metal layer and the second metal layer.

40. The plasmon sensor according to claim 31, further comprising an alternating-current (AC) power source that applied an AC voltage between the first metal layer and the second metal layer.

41. The plasmon sensor according to claim 31, wherein the first metal layer is made of a metal.

42. The plasmon sensor according to claim 31, wherein a plurality of antibodies are configured to be disposed on at least one of a first adjacent region around the first metal layer and a second adjacent region around the second metal layer in the hollow space.

43. The plasmon sensor according to claim 42, wherein the plurality of antibodies are configured to be disposed on at least one of the lower surface of the first metal layer and the upper surface of the second metal layer.

* * * * *